United States Patent

Bulliard et al.

[11] Patent Number: 6,117,997
[45] Date of Patent: Sep. 12, 2000

[54] HYDROXYPHENYLTRIAZINES

[75] Inventors: Christophe Bulliard, Fribourg; Thomas Schäfer, Basel; Christian Zumwald, Riehen, all of Switzerland

[73] Assignee: Ciba Specialty Chemicals Corporation, Tarrytown, N.Y.

[21] Appl. No.: 09/312,799

[22] Filed: May 17, 1999

Related U.S. Application Data

[63] Continuation-in-part of application No. 08/974,263, Nov. 19, 1997.

[51] Int. Cl.⁷ .................................................. C07D 251/24
[52] U.S. Cl. ................................................... 544/216
[58] Field of Search ............................................... 544/216

[56] References Cited

U.S. PATENT DOCUMENTS

| | | | |
|---|---|---|---|
| 3,113,940 | 12/1963 | Johns et al. | 260/248 |
| 3,113,941 | 12/1963 | Johns et al. | 260/248 |
| 3,113,942 | 12/1963 | Johns et al. | 260/248 |
| 3,118,887 | 1/1964 | Hardy et al. | 260/248 |
| 3,242,175 | 3/1966 | Duennenberger et al. | 260/248 |
| 3,244,708 | 4/1966 | Duennenberger et al. | 360/248 |
| 3,249,608 | 5/1966 | Biland et al. | 260/248 |
| 3,843,371 | 10/1974 | Piller et al. | 96/84 |
| 4,619,956 | 10/1986 | Susi | 524/87 |
| 4,826,978 | 5/1989 | Migdal et al. | 544/216 |
| 5,300,414 | 4/1994 | Leppard et al. | 544/215 |
| 5,364,749 | 11/1994 | Leppard et al. | 430/507 |
| 5,461,151 | 10/1995 | Waterman | 544/216 |
| 5,489,503 | 2/1996 | Toan | 430/507 |
| 5,538,840 | 7/1996 | Van Toan et al. | 430/5.2 |
| 5,545,836 | 8/1996 | Reinehr et al. | 544/216 |
| 5,591,850 | 1/1997 | Birbaum et al. | 544/216 |
| 5,597,854 | 1/1997 | Birbaum et al. | 524/100 |

FOREIGN PATENT DOCUMENTS

| | | |
|---|---|---|
| 0 434 608 | 6/1991 | European Pat. Off. . |
| 434608 | 6/1991 | European Pat. Off. . |
| 0530135 | 3/1993 | European Pat. Off. . |
| 0685223 | 12/1995 | European Pat. Off. . |
| 704437 | 4/1996 | European Pat. Off. . |
| 0878469 | 11/1998 | European Pat. Off. . |
| 1001381 | 10/1995 | Netherlands . |
| 484695 | 3/1970 | Switzerland . |
| 975966 | 11/1964 | United Kingdom . |
| 1321561 | 6/1973 | United Kingdom . |
| 2286774 | 8/1995 | United Kingdom . |
| 2294043 | 4/1996 | United Kingdom . |
| 2319523 | 5/1998 | United Kingdom . |
| 2312210 | 8/1998 | United Kingdom . |
| 94/05645 | 3/1994 | WIPO . |
| 94/18278 | 8/1994 | WIPO . |
| 96/28431 | 9/1996 | WIPO . |
| 97/03642 | 2/1997 | WIPO . |
| 97/03643 | 2/1997 | WIPO . |
| 99/26934 | 6/1999 | WIPO . |

OTHER PUBLICATIONS

Abstract for EP 0878469, Nov. 1998.
Abstract for EP 0685223, Dec. 1995.
Chem. Abstr. 119:213920n for EP 530135, 1993.
Chem. Abstr. 72:121590n for CH 484695, 1970.

*Primary Examiner*—Richard L. Raymond
*Assistant Examiner*—Venkataraman Balasubramanian
*Attorney, Agent, or Firm*—Luther A.R. Hall; Tyler A. Stevenson

[57] ABSTRACT

A description is given of compounds of the formula

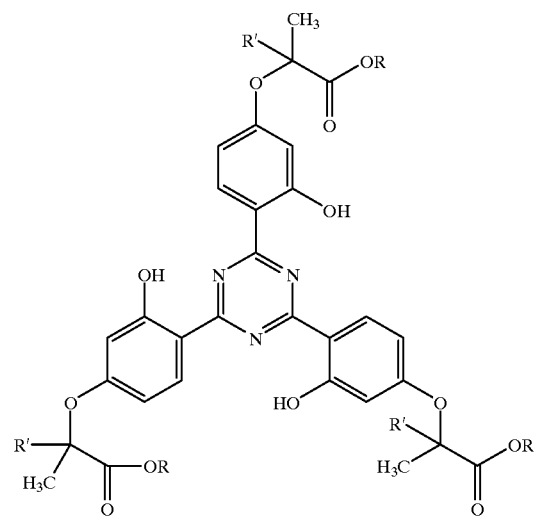

wherein R and R' independently are H, methyl or ethyl.

The novel compounds are effective as stabilizers for organic material against the damaging effect of light, oxygen and heat; they are also suitable for use in skin or hair protection preparations.

3 Claims, No Drawings

HYDROXYPHENYLTRIAZINES

This is a continuation-in-part of application Ser. No. 08/974263, filed Nov. 19, 1997.

The invention relates to novel compounds of the hydroxyphenyl-s-triazine type, to the use of these compounds for stabilizing organic material, especially in photographic material, plastics, coating materials, cosmetic preparations, sun screen lotions, against damage by light, oxygen and/or heat, and to correspondingly stabilized organic material.

When it is desired to increase the stability of an organic material, especially a coating, to light, it is common to add a light stabilizer. One very frequently employed class of light stabilizers are the UV absorbers, which protect the material by absorbing the harmful radiation via chromophores. One important group of UV absorbers are the triphenyl-s-triazines, as are described, inter alia, in the publications U.S. Pat. No. 3,118,887, U.S. Pat. No. 3,242,175, U.S. Pat. No. 3,244,708, GB-A-1 321 561, EP-A-0 434 608, U.S. Pat. No. 4,619, 956, U.S. Pat. No. 5,364,749, U.S. Pat. No. 5,461,151, EP-A-0 704 437 and WO-96/28431.

Also known are individual compounds of the hydroxyphenyl-s-triazine type some or all of whose hydroxyl groups in ortho position are blocked (U.S. Pat. No. 3,113,940, U.S. Pat. No. 3,113,941, U.S. Pat. No. 3,113,942, GB-A-975 966, U.S. Pat. No. 3,249,608, U.S. Pat. No. 5,597,854, WO-94/05645).

Specific compounds from the class of the trisaryl-s-triazines have now been found which, surprisingly, possess particularly good stabilizer properties. The invention therefore provides a compound of the formula I

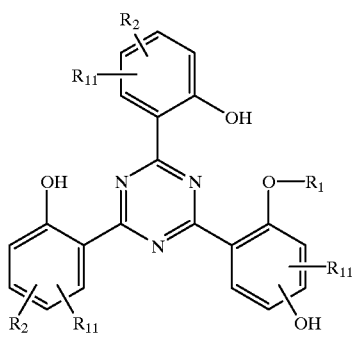

in which $R_1$ is $C_1-C_{18}$alkyl; $C_5-C_{12}$cycloalkyl; $C_3-C_{18}$alkenyl; phenyl; $C_1-C_{18}$alkyl which is substituted by phenyl, OH, $C_1-C_{18}$alkoxy, $C_5-C_{12}$cycloalkoxy, $C_3-C_{18}$alkenyloxy, halogen, —COOH, —COOR$_4$, —O—CO—R$_5$, —O—CO—O—R$_6$, —CO—NH$_2$, —CO—NHR$_7$, —CO—N(R$_7$)(R$_8$), CN, NH$_2$, NHR$_7$, —N(R$_7$)(R$_8$), —NH—CO—R$_5$, phenoxy, $C_1-C_{18}$alkyl-substituted phenoxy, phenyl-$C_1-C_4$alkoxy, $C_6-C_{15}$bicycloalkoxy, $C_6-C_{15}$bicycloalkylalkoxy, $C_6-C_{15}$bicycloalkenylalkoxy, or $C_6-C_{15}$tricycloalkoxy; $C_5-C_{12}$cycloalkyl which is substituted by OH, $C_1-C_4$alkyl, $C_2-C_6$alkenyl or —O—CO—R$_5$; —CO—R$_9$ or —SO$_2$—R$_{10}$; or $R_1$ is $C_3-C_{50}$alkyl which is interrupted by one or more oxygen atoms and/or substituted by OH, phenoxy or $C_7-C_{18}$alkylphenoxy; or $R_1$ is one of the definitions —A; —CH$_2$—CH(XA)—CH$_2$—O—R$_{12}$; —CR$_{13}$R'$_{13}$—(CH$_2$)$_m$—X—A; —CH$_2$—CH(OA)—R$_{14}$; —CH$_2$—CH(OH)—CH$_2$—XA;

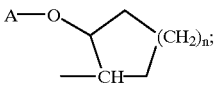

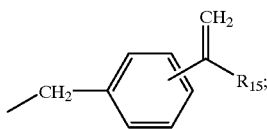

—CR$_{15}$R'$_{15}$—C(=CH$_2$)—R"$_{15}$; —CR$_{13}$R'$_{13}$—(CH$_2$)$_m$—CO—X—A; —CR$_{13}$R'$_{13}$—(CH$_2$)$_m$—CO—O—CR$_{15}$R'$_{15}$—C(=CH$_2$)—R"$_{15}$ or —CO—O—CR$_{15}$R'$_{15}$—C(=CH$_2$)—R"$_{15}$, where A is —CO—CR$_{16}$=CH—R$_{17}$; the radicals $R_2$, independently of one another, are $C_6-C_{18}$alkyl; $C_2-C_6$alkenyl; phenyl; $C_7-C_{11}$-phenylalkyl; COOR$_4$; CN; NH—CO—R$_5$; halogen; trifluoromethyl; —O—R$_3$; $R_3$ embraces the definitions given for $R_1$; $R_4$ is $C_1-C_{18}$alkyl; $C_3-C_{18}$alkenyl; phenyl; $C_7-C_{11}$phenylalkyl; $C_5-C_{12}$cycloalkyl; or is $C_3-C_{50}$alkyl, which is interrupted by one or more —O—, —NH—, —NR$_7$—, —S— and can be substituted by OH, phenoxy or $C_7-C_{18}$alkylphenoxy; $R_5$ is H; $C_1-C_{18}$alkyl; $C_2-C_{18}$alkenyl; $C_5-C_{12}$cycloalkyl; phenyl; $C_7-C_{11}$phenylalkyl; $C_6-C_{15}$bicycloalkyl; $C_6-C_{15}$bicycloalkenyl; $C_6-C_{15}$tricycloalkyl; $R_6$ is H; $C_1-C_{18}$alkyl; $C_3-C_{18}$alkenyl; phenyl; $C_7-C_{11}$phenylalkyl; $C_5-C_{12}$cycloalkyl; $R_7$ and $R_8$, independently of one another are $C_1-C_{12}$alkyl; $C_3-C_{12}$alkoxyalkyl; $C_4-C_{16}$dialkylaminoalkyl; or are $C_5-C_{12}$cycloalkyl; or together are $C_3-C_9$alkylene, $C_3-C_9$oxaalkylene or $C_3-C_9$azaalkylene; $R_9$ is $C_1-C_{18}$alkyl; $C_2-C_{18}$alkenyl; phenyl; $C_5-C_{12}$cycloalkyl; $C_7-C_{11}$phenylalkyl; $C_6-C_{15}$bicycloalkyl, $C_6-C_{15}$bicycloalkylalkyl, $C_6-C_{15}$bicycloalkenyl, or $C_6-C_{15}$tricycloalkyl; $R_{10}$ is $C_1-C_{12}$alkyl; phenyl; naphthyl or $C_7-C_{14}$alkylphenyl; the radicals $R_{11}$ independently of one another are H; $C_1-C_{18}$alkyl; $C_3-C_6$alkenyl; phenyl; $C_7-C_{11}$phenylalkyl; halogen; $C_1-C_{18}$alkoxy; $R_{12}$ is $C_1-C_{18}$alkyl; $C_3-C_{18}$alkenyl; phenyl; phenyl which is substituted by one to three radicals $C_1-C_8$alkyl, $C_1-C_8$alkoxy, $C_3-C_8$alkenoxy, halogen or trifluoromethyl; or is $C_7-C_{11}$phenylalkyl; $C_5-C_{12}$cycloalkyl; $C_6-C_{15}$tricycloalkyl; $C_6-C_{15}$bicycloalkyl; $C_6-C_{15}$bicycloalkylalkyl; $C_6-C_{15}$bicycloalkenylalkyl; —CO—R$_5$; or is $C_3-C_{50}$alkyl which is interrupted by one or more —O—, —NH—, —NR$_7$—, —S— and can be substituted by OH, phenoxy or $C_7-C_{18}$alkylphenoxy; $R_{13}$ and $R'_{13}$ independently of one another are H; $C_1-C_{18}$alkyl; phenyl; $R_{14}$ is $C_1-C_{18}$alkyl; $C_3-C_{12}$alkoxyalkyl; phenyl; phenyl-$C_1-C_4$alkyl; $R_{15}$, $R'_{15}$ and $R''_{15}$ independently of one another are H or CH$_3$; $R_{16}$ is H; —CH$_2$—COO—R$_4$; $C_1-C_4$alkyl; or CN; $R_{17}$ is H; —COOR$_4$; $C_1-C_{17}$alkyl; or phenyl; X is —NH—; —NR$_7$—; —O—; —NH—(CH$_2$)$_p$—NH—; or —O—(CH$_2$)$_q$—NH—; and the indices m is a number 0–19; n is a number 1–8; p is a number 0–4; and q is a number 2–4;
where at least one of the radicals $R_1$, $R_2$ and $R_{11}$ in formula I contains 2 or more carbon atoms. Preferably, at least one of the radicals $R_1$, $R_2$, $R_{11}$ in formula I and in formula II below contains 3 or more carbon atoms, especially 4 or more carbon atoms.

Within the scope of the stated definitions the radicals $R_1$ to $R_{10}$, $R_{12}$ to $R_{14}$, $R_{16}$ and $R_{17}$ as alkyl are branched or unbranched alkyl, for example methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl.

The radicals $R_1$, $R_3$ to $R_9$ and $R_{12}$ as $C_5$–$C_{12}$cycloalkyl comprise cyclopentyl, cyclohexyl, cycloheptyl, cyclooctyl, cyclononyl, cyclodecyl, cycloundecyl, cyclododecyl. Preference is given to cyclopentyl, cyclohexyl, cyclooctyl and cyclododecyl.

Within the scope of the stated definitions, $R_1$ to $R_6$, $R_9$, $R_{11}$ and $R_{12}$ as alkenyl embrace, inter alia, allyl, isopropenyl, 2-butenyl, 3-butenyl, isobutenyl, n-penta-2,4-dienyl, 3-methylbut-2-enyl, n-oct-2-enyl, n-dodec-2-enyl, isododecenyl, n-dodec-2-enyl or n-octadec-4-enyl.

Substituted alkyl, cycloalkyl or phenyl radicals can be substituted one or more times and can carry substituents on the bonding carbon atom (in α-position) or on other carbon atoms; if the substituent bonds by means of a heteroatom (for example alkoxy) it is preferably not in α-position and the substituted alkyl radical contains 2, especially 3, or more carbon atoms. Two or more substituents bond preferably to different carbon atoms.

Alkyl interrupted by —O—, —NH—, —$NR_7$—, —S— can be interrupted by one or more of these groups, one group in each case being inserted, in general into one bond, and hetero-hetero bonds, for example O—O, S—S, NH—NH, etc., not occurring; if the interrupted alkyl is additionally substituted, the substituents are generally not α to the heteroatom. If two or more interrupting groups of the type —O—, —NH—, —$NR_7$—, —S— occur in one radical, they are usually identical.

Aryl is generally an aromatic hydrocarbon radical, for example phenyl, biphenylyl or naphthyl, preferably phenyl and biphenylyl. Aralkyl is generally alkyl substituted by aryl, especially by phenyl; thus $C_7$–$C_{20}$aralkyl comprises, for example, benzyl, α-methylbenzyl, phenylethyl, phenylpropyl, phenylbutyl, phenylpentyl and phenylhexyl; $C_7$–$C_{11}$phenylalkyl preferably embraces benzyl, α-methylbenzyl and α,α-dimethylbenzyl.

Alkylphenyl and alkylphenoxy are alkyl-substituted phenyl and phenoxy, respectively.

A halogen substituent is —F, —Cl, —Br or —I; preference is given to —F or —Cl, especially —Cl.

$C_1$–$C_{20}$alkylene is, for example, methylene, ethylene, propylene, butylene, pentylene, hexylene, etc. The alkyl chain here can also be branched, as in isopropylene, for example.

$C_4$–$C_{12}$cycloalkenyl is, for example 2-cyclobuten-1-yl, 2-cyclopenten-1-yl, 2,4-cyclopentadien-1-yl-, 2-cyclohexen-1-yl, 2-cyclohepten-1-yl or 2-cycloocten-1-yl.

$C_6$–$C_{15}$bicycloalkyl is, for example, bornyl, norbornyl, [2.2.2]bicyclooctyl. Preference is given to bornyl and norbornyl, especially bornyl and norborn-2-yl.

$C_6$–$C_{15}$bicycloalkoxy is, for example, bornyloxy or norborn-2-yloxy.

$C_6$–$C_{15}$bicycloalkyl-alkyl or -alkoxy is bicycloalkyl-substituted alkyl or alkoxy, the total number of carbon atoms being 6–15; examples are norbornane-2-methyl and norbornyl-2-methoxy.

$C_6$–$C_{15}$bicycloalkenyl is, for example, norbornenyl, norbornadienyl. Preference is given to norbornenyl, especially norborn-5-ene.

$C_6$–$C_{15}$bicycloalkenylalkoxy is bicycloalkenyl-substituted alkoxy, the total number of carbon atoms being 6–15; one example is norborn-5-ene-2-methoxy.

$C_6$–$C_{15}$tricycloalkyl is, for example, 1-adamantyl, 2-adamantyl. Preference is given to 1-adamantyl.

$C_6$–$C_{15}$tricycloalkoxy is, for example, adamantyloxy.

$C_3$–$C_{12}$heteroaryl is, preferably, pyridinyl, pyrimidinyl, triazinyl, pyrrolyl, furanyl, thiophenyl or quinolinyl.

Typical compounds of the formula I comprise those in which $R_1$ is $C_1$–$C_{18}$alkyl; $C_5$–$C_{12}$cycloalkyl; $C_3$–$C_{12}$alkenyl; phenyl; $C_1$–$C_{18}$alkyl which is substituted by phenyl, OH, $C_1$–$C_{18}$alkoxy, $C_5$–$C_{12}$cycloalkoxy, $C_3$–$C_{18}$alkenyloxy, halogen, —COOH, —COO$R_4$, —O—CO—$R_5$, —O—CO—O—$R_6$, —CO—$NH_2$, —CO—$NHR_7$, —CO—$N(R_7)(R_8)$, CN, $NH_2$, $NHR_7$, —$N(R_7)(R_8)$, —NH—CO—$R_5$, phenoxy, $C_1$–$C_{18}$alkyl-substituted phenoxy, phenyl-$C_1$–$C_4$alkoxy, bornyloxy, norborn-2-yloxy, norbornyl-2-methoxy, norborn-5-ene-2-methoxy, adamantyloxy; $C_5$–$C_{12}$cycloalkyl which is substituted by OH, $C_1$–$C_4$alkyl, $C_2$–$C_6$alkenyl and/or —O—CO—$R_5$; glycidyl; —CO—$R_9$ or —$SO_2$—$R_{10}$; or $R_1$ is $C_3$–$C_{50}$alkyl which is interrupted by one or more oxygen atoms and/or is substituted by OH, phenoxy or $C_7$–$C_{18}$alkylphenoxy; or $R_1$ is one of the definitions —A; —$CH_2$—CH(XA)—$CH_2$—O—$R_{12}$; —$CR_{13}R'_{13}$—$(CH_2)_m$—X—A; —$CH_2$—CH(OA)—$R_{14}$; —$CH_2$—CH(OH)—$CH_2$—XA;

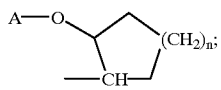

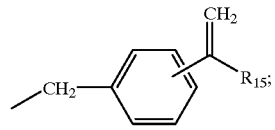

—$CR_{15}R'_{15}$—C(=$CH_2$)—$R''_{15}$; —$CR_{13}R'_{13}$—$(CH_2)_m$—CO—X—A; —$CR_{13}R'_{13}$—$(CH_2)_m$—CO—O—$CR_{15}R'_{15}$—C(=$CH_2$)—$R''_{15}$ or —CO—O—$CR_{15}R'_{15}$—C(=$CH_2$)—$R''_{15}$, where A is —CO—$CR_{16}$=CH—$R_{17}$; the radicals $R_2$ are $C_6$–$C_{18}$alkyl; $C_2$–$C_6$alkenyl; phenyl; —O—$R_3$ or —NH—CO—$R_5$ and the radicals $R_3$ independently of one another embrace the definitions given for $R_1$; $R_4$ is $C_1$–$C_{18}$alkyl; $C_3$–$C_{18}$alkenyl; phenyl; $C_7$–$C_{11}$phenylalkyl; $C_5$–$C_{12}$cycloalkyl; or is $C_3$–$C_{50}$alkyl, which is interrupted by one or more —O—, —NH—, —$NR_7$—, —S— and can be substituted by OH, phenoxy or $C_7$–$C_{18}$alkylphenoxy; $R_5$ is H; $C_1$–$C_{18}$alkyl; $C_2$–$C_{18}$alkenyl; $C_5$–$C_{12}$cycloalkyl; phenyl; $C_7$–$C_{11}$phenylalkyl; norborn-2-yl; norborn-5-en-2-yl; adamantyl; $R_6$ is H; $C_1$–$C_{18}$alkyl; $C_3$–$C_{18}$alkenyl; phenyl; $C_7$–$C_{11}$phenylalkyl; $C_5$–$C_{12}$cycloalkyl; $R_7$ and $R_8$ independently of one another are $C_1$–$C_{12}$alkyl; $C_3$–$C_{12}$alkoxyalkyl; $C_4$–$C_{16}$dialkylaminoalkyl; or are $C_5$–$C_{12}$cycloalkyl; or together are $C_3$–$C_9$alkylene, $C_3$–$C_9$oxaalkylene or $C_3$–$C_9$azaalkylene; $R_9$ is $C_1$–$C_{18}$alkyl; $C_2$–$C_{18}$alkenyl; phenyl; $C_5$–$C_{12}$cycloalkyl; $C_7$–$C_{11}$phenylalkyl; norborn-2-yl; norborn-5-en-2-yl; adamantyl; $R_{10}$ is $C_1$–$C_{12}$alkyl; phenyl; naphthyl or $C_7$–$C_{14}$alkylphenyl; the radicals $R_{11}$ independently of one another are H; $C_1$–$C_{18}$alkyl; or $C_7$–$C_{11}$phenylalkyl; $R_{12}$ is $C_1$–$C_{18}$alkyl; $C_3$–$C_{18}$alkenyl; phenyl; phenyl which is substituted by one to three $C_1$–$C_8$alkyl, $C_1$–$C_8$alkoxy, $C_3$–$C_8$alkenoxy, halogen or trifluoromethyl; or is $C_7$–$C_{11}$phenylalkyl; $C_5$–$C_{12}$cycloalkyl; 1-adamantyl; 2-adamantyl; norbornyl; norbornane-2-methyl-; —CO—$R_5$; or is $C_3$–$C_{50}$alkyl which is interrupted by one or more —O—, —NH—, —$NR_7$—, —S— and can be substituted by OH, phenoxy or $C_7$–$C_{18}$alkylphenoxy; $R_{13}$ and $R'_{13}$ independently of one another are H; $C_1$–$C_{18}$alkyl; phenyl; $R_{14}$ is $C_1$–$C_{18}$alkyl; $C_3$–$C_{12}$alkoxyalkyl; phenyl; phenyl-$C_1$–$C_4$alkyl; $R_{15}$, $R'_{15}$ and $R''_{15}$ independently of one another are H or $CH_3$; $R_{16}$ is H; —$CH_2$—COO—$R_4$; $C_1$–$C_4$alkyl; or CN; $R_{17}$ is H; —COOR$_4$; $C_1$–$C_{17}$alkyl; or phenyl; X is —NH—; —NR$_7$—; —O—; —NH—(CH$_2$)$_p$—NH—; or —O—(CH$_2$)$_q$—NH—; and the indices m is a number 0–19; n is a number 1–8; p is a number 0–4; and q is a number 2–4; especially those of the formula II

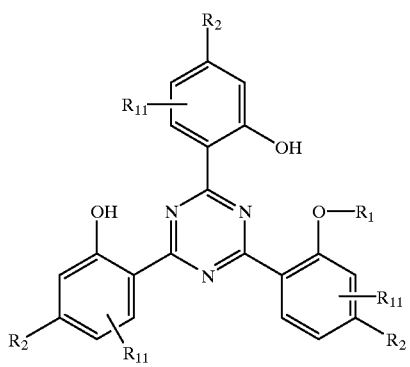

(II)

in which $R_1$, $R_2$ and $R_{11}$ are as defined above.

Among the compounds of the formula II preference is given to those in which the radicals $R_2$ are identical, especially to those in which the radicals $R_2$ have the definition —O—$R_3$, and in particular to those in which $R_{11}$ is H.

Compounds of the formulae I or II comprising a polymerizable double bond, and of these—especially those in which R, and/or $R_3$ are/is a radical —A; —CH$_2$—CH(XA)—CH$_2$—O—$R_{12}$; —CR$_{13}$R'$_{13}$—(CH$_2$)$_m$—X—A; —CH$_2$—CH(OA)—$R_{14}$; —CH$_2$—CH(OH)—CH$_2$—XA;

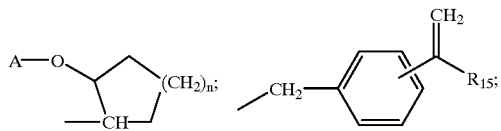

CR$_{13}$R'$_{13}$—(CH$_2$)$_m$—CO—X—A; —CR$_{13}$R'$_{13}$—(CH$_2$)$_m$—CO—O—CR$_{15}$R'$_{15}$—C(=CH$_2$)—R''$_{15}$ or —CO—O—CR$_{15}$R'$_{15}$—C(=CH$_2$)—R''$_{15}$ or $C_5$–$C_{12}$cycloalkyl which is substituted by $C_2$–$C_6$alkenyl, by OH and $C_2$–$C_6$alkenyl, or by —O—CO—R$_5$, where R$_5$ is $C_2$–$C_3$alkenyl and A is —CO—CR$_{16}$=CH—R$_{17}$, constitute a subject of special interest.

In particularly preferred compounds, X is —O—. Preferably, in such compounds, $R_{12}$ is $C_1$–$C_{18}$alkyl or $C_5$–$C_{12}$cycloalkyl; $R_{13}$ is H or $C_1$–$C_{18}$alkyl; $R'_{13}$ is H; $R_{16}$ is H or methyl; $R_{17}$ is H.

Preference is given to compounds of the formula II in which $R_1$ is $C_1$–$C_{18}$alkyl; $C_5$–$C_{12}$cycloalkyl; phenyl; $C_1$–$C_{18}$alkyl which is substituted by phenyl, OH, $C_1$–$C_{18}$alkoxy, $C_5$–$C_{12}$cycloalkoxy, —COOH, —COOR$_4$, —O—CO—R$_5$, phenyl-$C_1$–$C_4$alkoxy; or is cyclohexyl which is substituted by OH, $C_1$–$C_4$alkyl, $C_2$–$C_6$alkenyl and/or —O—CO—R$_5$; or $R_1$ is one of the definitions —A; —CH$_2$—CH(XA)—CH$_2$—O—$R_{12}$; —CR$_{13}$R'$_{13}$—(CH$_2$)$_m$—X—A; —CH$_2$—CH(OA)—R$_{14}$; —CH$_2$—CH(OH)—CH$_2$—XA;

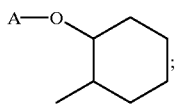

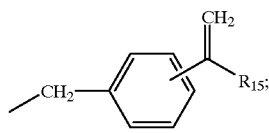

—CR$_{15}$R'$_{15}$—C(=CH$_2$)—R''$_{15}$; —CR$_{13}$R'$_{13}$—(CH$_2$)$_m$—CO—X—A; Glycidyl; —CR$_{13}$R'$_{13}$—(CH$_2$)$_m$—CO—O—CR$_{15}$R'$_{15}$C(=CH$_2$)—R''$_{15}$ or —CO—O—CR$_{15}$R'$_{15}$—C(=CH$_2$)—R''$_{15}$, where A is —CO—CR$_{16}$=CH—R$_{17}$; the radicals $R_2$ are —O—$R_3$ or —NH—CO—R$_5$ and the radicals $R_3$ independently of one another embrace the definitions given for $R_1$; $R_4$ is $C_1$–$C_{18}$alkyl; $C_7$–$C_{11}$phenylalkyl; cyclohexyl; or $C_3$–$C_{50}$alkyl which is interrupted by —O— and can be substituted by OH, phenoxy or $C_7$–$C_{18}$alkylphenoxy; $R_5$ is $C_1$–$C_{18}$alkyl; cyclohexyl; phenyl; $C_7$–$C_{11}$phenylalkyl; $R_7$ is $C_1$–$C_{12}$alkyl or cyclohexyl; $R_{11}$ is H; $R_{12}$ is $C_1$–$C_{18}$alkyl; phenyl; $C_1$–$C_8$alkyl- or $C_1$–$C_8$alkoxy-substituted phenyl; $C_7$–$C_{11}$ phenylalkyl $C_5$–$C_{12}$cycloalkyl; —CO—R$_5$; or is $C_3$–$C_{50}$alkyl which is interrupted by —O— and can be substituted by OH, phenoxy or $C_7$–$C_{18}$alkylphenoxy; $R_{13}$ is H; $C_1$–$C_{18}$alkyl; phenyl; $R'_{13}$ is H; $R_{14}$ is $C_1$–$C_{18}$alkyl; phenyl; phenyl-$C_1$–$C_4$alkyl; $R_{15}$, $R'_{15}$ and $R''_{15}$ independently of one another are H or $CH_3$; $R_{16}$ is H; —CH$_2$—COO—R$_4$; $C_1$–$C_4$alkyl; or CN; $R_{17}$ is H; —COOR$_4$; $C_1$–$C_{17}$alkyl; or phenyl; X is —NH—; —NR$_7$—; or —O—; and m is a number 0–19.

Particularly preferred compounds of the formula II are those in which $R_1$ is $C_1$–$C_{18}$alkyl; $C_5$–$C_{12}$cycloalkyl; $C_1$–$C_{18}$alkyl which is substituted by phenyl, OH, $C_1$–$C_{18}$alkoxy, —COOR$_4$, —O—CO—R$_5$; or cyclohexyl which is substituted by OH, $C_1$–$C_4$alkyl, $C_2$–$C_6$alkenyl; or $R_1$ is one of the definitions —A; —CH$_2$—CH(XA)—CH$_2$—O—$R_{12}$; —CR$_{13}$R'$_{13}$—(CH$_2$)$_m$—X—A; —CH$_2$—CH(OA)—R$_{14}$; —CH$_2$—CH(OH)—CH$_2$—XA;

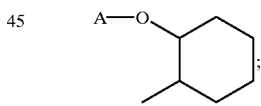

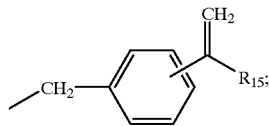

—CR$_{15}$R'$_{15}$—C(=CH$_2$)—R''$_{15}$; —CR$_{13}$R'$_{13}$—(CH$_2$)$_m$—CO—X—A; —CR$_{13}$R'$_{13}$—(CH$_2$)$_m$—CO—O—CR$_{15}$R'$_{15}$—C(=CH$_2$)—R''$_{15}$ or —CO—O—CR$_{15}$R'$_{15}$—C(=CH$_2$)—R'$_{15}$ where A is —CO—CR$_{16}$=CH—R$_{17}$; the radicals $R_2$ are —O—$R_3$ or —NH—CO—R$_5$ and the radicals $R_3$ independently of one another embrace the definitions given for $R_1$; $R_4$ is $C_1$–$C_{18}$alkyl; $C_7$–$C_{11}$phenylalkyl or cyclohexyl; $R_5$ is $C_1$–$C_{18}$alkyl; $R_{11}$ is H; $R_{12}$ is $C_1$–$C_{18}$alkyl; $C_7$–$C_{11}$phenylalkyl; $C_5$–$C_{12}$cycloalkyl; —CO—R$_5$; $R_{13}$ is H or $C_1$–$C_{18}$alkyl; $R'_{13}$ is H; $R_{14}$ is $C_1$–$C_{18}$alkyl; $R_{15}$, $R'_{15}$, $R''_{15}$, $R_{16}$ and $R_{17}$ independently of one another are H or $CH_3$; X is —O—; and m is a number 0–19.

Of especial interest are compounds of the formula II in which $R_2$ is —$OR_3$, $R_1$ and $R_3$ independently of one another are $C_1$–$C_{18}$alkyl; or are $C_2$–$C_6$alkyl which is substituted by OH, $C_1$–$C18$alkoxy and/or —$COOR_4$; or are $CH_2COOR_4$; or are cyclohexyl which is unsubstituted or substituted by OH and/or $C_2$–$C_3$alkenyl; and $R_4$ is $C_1$–$C_6$alkyl; and $R_{11}$ is hydrogen.

Of particular technical interest are those compounds of the formula II in which $R_2$ is —$OR_3$, $R_1$ and $R_3$ independently of one another are $C_1$–$C_{18}$alkyl, especially branched $C_5$–$C_{18}$alkyl; and $R_{11}$ is hydrogen. These compounds are particularly suitable for use as UV filters in cosmetic, pharmaceutical and veterinary preparations.

To prepare compounds of the formula I and especially of the formula II it is judicious to start from compounds of the formula A and, respectively, of the formula A',

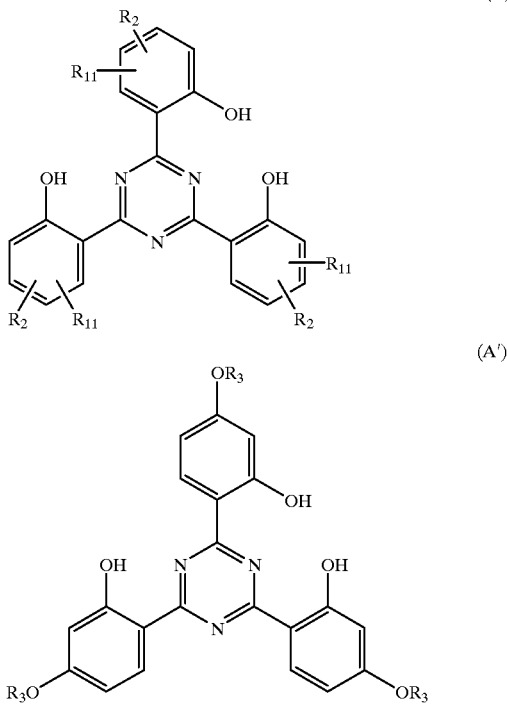

in which the radicals $R_2$ independently of one another are $C_6$–$C_{18}$alkyl; $C_2$–$C_6$alkenyl; phenyl; $C_7$–$C_{11}$phenylalkyl; COOH; $COOR_4$; CN; NH—CO—$R_5$; halogen; trifluoromethyl; or —$OR_3$; and $R_3$, $R_4$, $R_5$ and $R_{11}$ have the definitions given for formula I, $R_3$ additionally embracing H.

Compounds of the formulae A and A' are known or can be obtained in analogy to known compounds by common methods, for example in accordance with or in analogy to one of the methods given in EP-A-434 608 or in the publication by H. Brunetti and C. E. Lüthi, Helv. Chim. Acta 55, 1566 (1972), by Friedel-Crafts addition of halotriazines onto corresponding phenols. This can be followed by a further reaction in accordance with known methods, for example for esterifying free carboxyl groups to give esters in which $R_2$ is $COOR_4$. Further details on starting compounds which can be used and on their preparation can be found in the literature cited at the outset and in EP-A-1 65 608.

Other methods of preparing starting compounds of the formula A are described by Cousin and Volmar, Bull. Soc. Chim. Fr. 15, 414–421 (1914), U.S. Pat. No. 3,113,942 or EP-A-648753; in accordance with or in analogy to these methods it is possible to trimerize 3 equivalents of a 2-hydroxybenzonitrile of the formula B

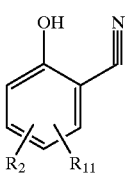

or of a 2-hydroxybenzamide of the formula C

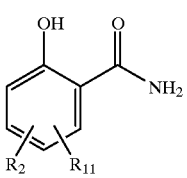

at elevated temperature, usually in the range 180–260° C., to give the compound of the formula A. This route is particularly suitable for compounds of the formula A in which $R_2$ is not OH or $OR_3$.

A particularly preferred starting compound of the formula A is tris(2,4-dihydroxyphenyl)-1,3,5-triazine; the novel compounds obtainable therefrom by preparation methods indicated below correspond to the formula II in which $R_2$ is —$OR_3$ and $R_{11}$ is hydrogen.

Options for the further reaction of the compound of the formula A to the compound of the formula I, and especially of the formula II, include the following:

a) Stepwise reaction of free OH groups with halides or sulfates

This is done using, for each OH to be reacted, about one equivalent of a reagent $R_1$—Hal in which Hal is a halogen atom, preferably Cl, and $R_1$ embraces the definitions given in connection with formula I above, together with about one equivalent of base. $R_1$—Hal can also be a mixture of reagents. Instead of the halide $R_1$—Hal it is also possible to use one equivalent of a sulfate (½ $R_1$—O—$SO_2$—O—$R_1$). If the intention is to introduce not only the radical —$R_1$ but also another, different radical ($R_2$ in the definition of —$OR_3$) then it is judicious first of all to carry out reaction with the required number of equivalents of $R_3$—Hal, where $R_3$ embraces the definitions given for $R_1$, and base and then reaction with one equivalent of $R_1$—Hal.

The reaction is preferably carried out in an organic solvent, for example an aromatic or aliphatic hydrocarbon, alcohol, ether, ester or amide of appropriate boiling range; preferred solvents are toluene, xylene, propanol, butanol, 2-methoxyethanol, 2-ethoxyethanol, diethylene glycol dimethyl ether (diglyme), dimethylformamide (DMF), dimethyl sulfoxide (DMSO). Suitable bases are organic or, preferably, inorganic bases such as hydroxides, oxides or carbonates; important examples are alkali metal hydroxides and carbonates, such as KOH, NaOH, $K_2CO_3$, $Na_2CO_3$. The reaction temperature is usually in the range 80–180° C., preferably in the range 100–150° C. The reaction can also be carried out as a 2-phase reaction in the presence of phase transfer catalysts such as tetraalkylammonium salts, for example; in this case the halide or sulfate is usually—and especially when it is employed as a pure alkylating reagent—present in the organic phase and the triazine precursor in the aqueous phase.

For instance, a compound of the formula II, in which $R_2$ is —$OR_3$ can be obtained, for example, by the following reaction schemes:

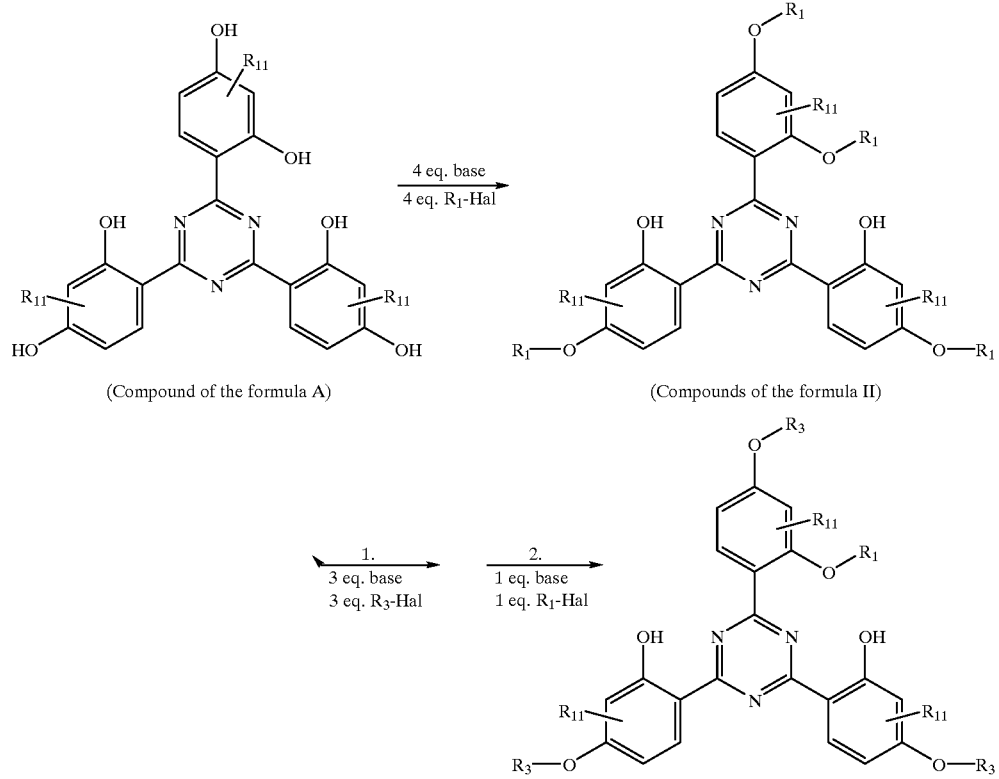

(Compound of the formula A)    (Compounds of the formula II)

b) Stepwise reaction of free OH groups with epoxides

Instead of the reagents described under a) it is also possible to employ epoxides. For each OH group to be reacted, in each case about 1 equivalent or more of an epoxide of the type

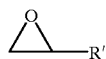

is employed, together with a catalyst, in bulk or in a solvent. This reaction usually takes place without the addition of bases. The primary reaction product of the formula I or II, in which $R_3$ or, if appropriate $R_3$ and $R_1$ correspond to the formula —$CH_2$—CH(OH)—R' can, if desired, be reacted further by known methods, for example with etherification or esterification of the aliphatic OH group.

If the intention is to introduce not only the radical —$R_3$ as —$CH_2$—CH(OH)—R' but also another, different radical $R_1$, then it is judicious first of all to carry out reaction with the required number of equivalents of

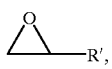

where usually no excess is used and where —$CH_2$—CH(OH)—R' embraces the definitions given for $R_1$, and then to carry out reaction with one equivalent of the desired further reagent, for example $R_1$—Hal and base, or with one further equivalent of

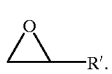

Conversely, in accordance with a) it is also possible first to introduce a radical —$R_3$ and then to react the reaction product with

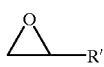

to give the compound of the formula I or II.

The ring opening of the epoxide is preferably carried out in an organic solvent, especially an apolar organic solvent; examples are aromatic or aliphatic hydrocarbons of appropriate boiling range, preferably toluene, xylene, mesitylene.

Examples of suitable catalysts are phase transfer catalysts, including quaternary phosphonium salts, or tertiary amines; e.g. ethyltriphenylphosphonium bromide or benzyldimethylamine.

The reaction temperature is usually in the range 80–200° C., preferably in the range 100–180° C.

For instance, a compound of the formula II in which $R_2$ is —$OR_3$ can be obtained, for example, by the following reaction schemes:

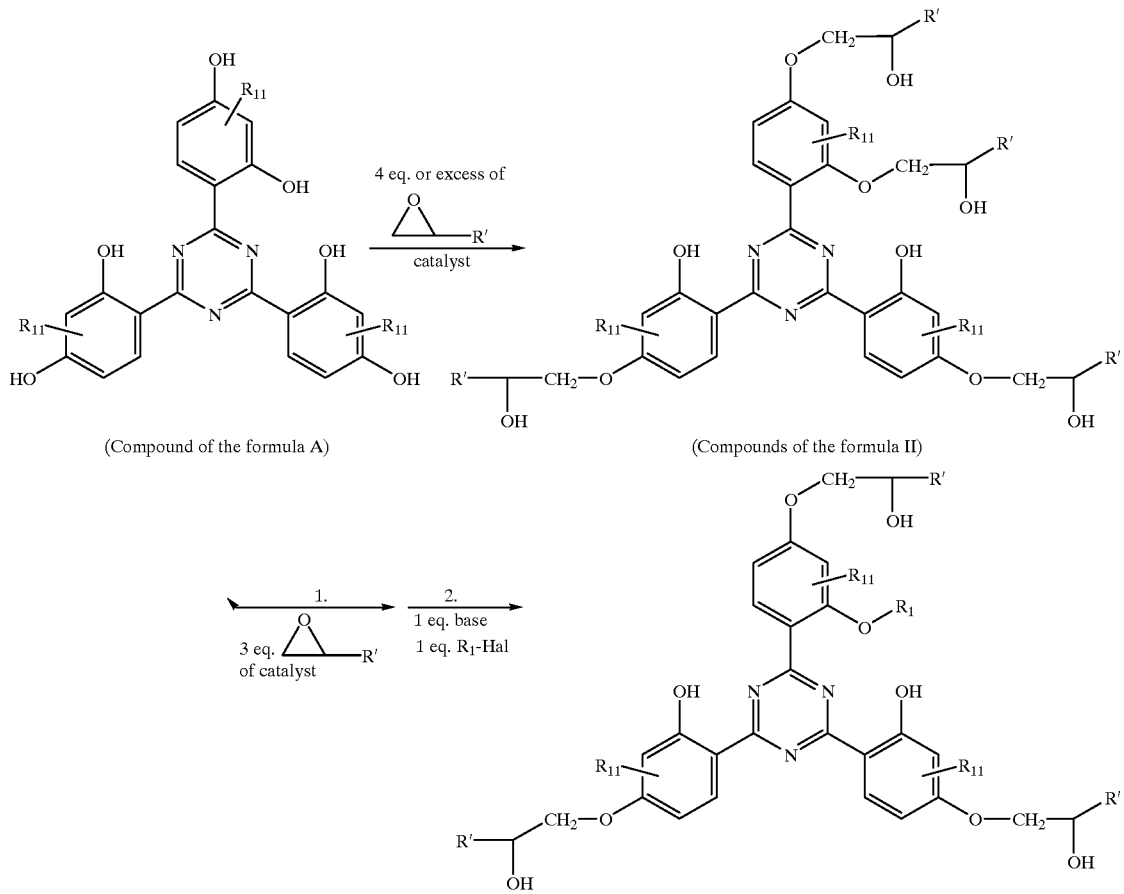

(Compound of the formula A)

(Compounds of the formula II)

The products of the above-described reactions can be modified further by known methods in the context of the definitions given for formula I.

The reactions can be carried out in the absence of oxygen, for example by flushing with an inert gas such as argon; however, in every case oxygen does not interfere, so that the reaction can also be carried out without this measure. After the end of the reaction, the product can be worked up by common methods.

The novel compounds are particularly suitable for stabilizing organic materials against damage by light, oxygen or heat. The novel compounds are especially suitable as light stabilizers (UV absorbers).

The materials to be stabilized can, for example, be oils, fats, waxes, coating materials, cosmetics, photographic materials or biocides. Of particular interest is their use in polymeric materials as are present in plastics, rubbers, coating materials, photographic materials or adhesives. When used in cosmetic preparations, the material to be protected is frequently not the preparation itself but skin or hair to which the preparation is applied.

Examples of polymers and other substrates which can be stabilized in this way are the following:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly($\alpha$-methylstyrene).

6. Copolymers of styrene or $\alpha$-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

7. Graft copolymers of styrene or $\alpha$-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from $\alpha,\beta$-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/ butadiene copolymers, acrylonitrile/alkyl acrylate copolymers, acrylonitrile/alkoxyalkyl acrylate or acrylonitrile/vinyl halide copolymers or acrylonitrile/ alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides, polyetherimids, polyesterimids, polyhydantoins and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.
19. Polycarbonates and polyester carbonates.
20. Polysulfones, polyether sulfones and polyether ketones.
21. Crosslinked polymers derived from aldehydes on the one hand and phenols, ureas and melamines on the other hand, such as phenol/formaldehyde resins, urea/formaldehyde resins and melamine/formaldehyde resins.
22. Drying and non-drying alkyd resins.
23. Unsaturated polyester resins derived from copolyesters of saturated and unsaturated dicarboxylic acids with polyhydric alcohols and vinyl compounds as crosslinking agents, and also halogen-containing modifications thereof of low flammability.
24. Crosslinkable acrylic resins derived from substituted acrylates, for example epoxy acrylates, urethane acrylates or polyester acrylates.
25. Alkyd resins, polyester resins and acrylate resins crosslinked with melamine resins, urea resins, isocyanates, isocyanurates, polyisocyanates or epoxy resins.
26. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.
27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.
28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

The invention therefore additionally provides a composition comprising A) an organic material which is sensitive to oxidative, thermal and/or actinic breakdown/buildup and B) as stabilizer at least one compound of the formula I, and also provides for the use of compounds of the formula I stabilizing organic material against oxidative, thermal or actinic breakdown/buildup. The invention likewise embraces a method of stabilizing organic material against thermal, oxidative and/or actinic breakdown/buildup, which comprises applying or adding at least one compound of the formula I to this material.

The amount of stabilizer to be used depends on the organic material to be stabilized and on the intended use of the stabilized material. In general the novel composition contains from 0.01 to 15, especially from 0.05 to 10 and, in particular, from 0.1 to 5 parts by weight of the stabilizer (component B) per 100 parts by weight of component A). The stabilizer (component B) can be an individual compound of the formula I or else a mixture.

In addition to the compounds of the formula I the novel compositions may comprise as additional component (C) one or more customary additives, for example antioxidants, other light stabilizers, metal passivators, phosphites or phosphonites. Examples of these are the following:

1. Antioxidants
   1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-($\alpha$-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.
   1.2. Alkylthiomethylthenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.
   1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl) adipate.
   1.4. Tocopherols, for example $\alpha$-tocopherol, $\beta$-tocopherol, $\gamma$-tocopherol, $\delta$-tocopherol and mixtures thereof (Vitamin E).
   1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis(2,6-dimethyl-4-hydroxyphenyl)disulfide.
   1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-($\alpha$-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-($\alpha$-methylbenzyl)-4-nonylphenol], 2,2'-methylenebis[6-($\alpha,\alpha$-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methylphenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy-2-methylphenyl)pentane.
   1.7. O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate.

1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine Compounds, for example 2,4-bis (octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris (3,5-di-tert-butyl-4-hydroxyphenoxy)-1,2,3-triazine, 1,3,5-tris-(3,5-di-tert-butyl-4-hydroxybenzyl)isocyanurate, 1,3,5-tris(4-tert-butyl-3-hydroxy-2,6-dimethylbenzyl) isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzyl phosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of β-(3,5-dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxythenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamide, N,N'-bis (3,5-di-tert-butyl-4-hydroxyphenylpropionyl) trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl]propionyloxy)ethyl]oxamide (Naugard®XL-1 supplied by Uniroyal).

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclo-hexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino) propane, (o-tolyl)biguanide, bis[4-(1',3'-dimethylbutyl) phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- und dialkylated tert-butyldiphenylamines, 2,3-dihydro-3,3-dimethyl-4H-1,4-benzothiazine, phenothiazine, a mixture of mono- und dialkylated tert-butyl/tert-octylphenothiazines, a mixture of mono- und dialkylated tert-octyl-phenothiazines, N-allylphenothiazin, N,N,N',N'-tetraphenyl-1,4-diaminobut-2-ene, N,N-bis(2,2,6,6-tetramethyl-piperid-4-yl-hexamethylenediamine, bis(2,2,6,6-tetramethylpiperid-4-yl)sebacate, 2,2,6,6-tetramethylpiperidin-4-one, 2,2,6,6-tetramethylpiperidin-4-ol.

2. UV absorbers and light stabilisers 2.1. 2-(2'-Hydroxyphenyl)benzotriazoles, for example 2-(2'-hydroxy-5'-methylphenyl)-benzotriazole, 2-(3',5'-di-2-(2'-hydroxy-5'-methylphenyl)benzotriazole, 2-(5'-tert-butyl-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chlorobenzotriazole, 2-(3'-sec-butyl-5'-tert-butyl-2'-hydroxyphenyl) benzotriazole, 2-(2'-hydroxy-4'-octyloxyphenyl)

benzotriazole, 2-(3',5'-di-tert-amyl-2'-hydroxyphenyl) benzotriazole, 2-(3',5'-bis-(α,α-dimethylbenzyl)-2'-hydroxyphenyl)benzotriazole, 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl) benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, 2-(3'-tert-butyl-2'-hydroxy-5'-(2-isooctyloxycarbonylethyl) phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO—CH$_2$CH$_2$-]$_2$ where R=3'-tert-butyl-4'-hydroxy-5'-2H-benzotriazol-2-ylphenyl, 2-[2'-hydroxy-3'-(α,α-dimethylbenzyl)-5'-(1,1,3,3-tetramethylbutyl)-phenyl]benzotriazole; 2-[2'-hydroxy-3'-(1,1,3,3-tetramethylbutyl)-5'-(α,α-dimethylbenzyl)-phenyl] benzotriazole.

2.2.2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutyl-phenyl salicylate, phenyl salicylate, octylphenyl salicylate, dibenzoyl resorcinol, bis (4-tert-butylbenzoyl) resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxy-cinnamate, butyl α-cyano-β-methyl-p-methoxy-cinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl) sebacate, bis(1-octyloxy-2,2,6,6-tetramethyl-4-piperidyl) sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl) hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1, 2,3,4-butane-tetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl- 1,3,8-triazaspiro[4.5]decan-2,4-dione, bis(1-octyloxy-2,2,6,6-tetramethylpiperidyl) sebacate, bis(1-octyloxy-2,2,6,6-tetramethylpiperidyl) succinate, linear or cyclic condensates of N,N'-bis-(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl) pyrrolidin-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensation product of N,N'-bis (2,2,6,6-tetramethyl-4-piperidyl)hexamethylenediamine and 4-cyclohexylamino-2,6-dichloro-1,3,5-triazine, a condensation product of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); N-(2,2,6,6-tetramethyl-4-piperidyl)-n-dodecylsuccinimid, N-(1,2,2,6,6-pentamethyl-4-piperidyl)-n-dodecylsuccinimid, 2-undecyl-7,7,9,9-tetramethyl-1-oxa-3,8-diaza-4-oxo-spiro [4,5]decane, a reaction product of 7,7,9,9-tetramethyl-2-cycloundecyl-1-oxa-3,8-diaza-4-oxospiro [4,5]decane und epichlorohydrin, 1,1-bis(1,2,2,6,6-pentamethyl-4-piperidyloxycarbonyl)-2-(4-methoxyphenyl)ethene, N,N'-bis-formyl-N,N'-bis(2,2,6,6-tetramethyl-4-piperidyl) hexamethylenediamine, diester of 4-methoxy-methylene-malonic acid with 1,2,2,6,6-pentamethyl-4-hydroxypiperidine, poly[methylpropyl-3-oxy-4-(2,2,6,6-tetramethyl-4-piperidyl)]siloxane, reaction product of maleic acid anhydride-α-olefin-copolymer with 2,2,6,6-tetramethyl-4-aminopiperidine or 1,2,2,6,6-pentamethyl-4-aminopiperidine.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis (2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxypropoxy) phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine, 2-[4-(dodecyloxy/tridecyloxy-2-hydroxypropoxy)-2-hydroxy-phenyl]-4,6-bis(2,4-dimethylphenyl)-1,3,5-triazine, 2-[2-hydroxy-4-(2- hydroxy-3-dodecyloxypropoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxypropoxy) phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl) hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl) oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, 6-fluoro-2,4,8,10-tetra-tert-butyl-12-methyl-dibenz[d,g]-1,3,2-dioxaphosphocin, bis(2,4-di-tert-butyl-6-methylphenyl) methyl phosphite, bis(2,4-di-tert-butyl-6-methylphenyl) ethyl phosphite, 2,2',2"-nitrilo[triethyltris(3,3',5,5'-tetra-tert-butyl-1,1'-biphenyl-2,2'-diyl)phosphite], 2-ethylhexyl(3,3',5,5'-tetra-tert-butyl-1,1'-biphenyl-2,2'-di-yl)phosphite.

Especially preferred are the following phosphites:

Tris(2,4-di-tert-butylphenyl) phosphite (Irgafos®168, Ciba-Geigy), tris(nonylphenyl) phosphate,

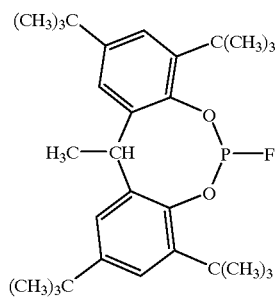

(A)

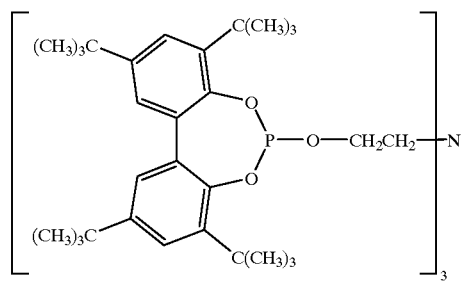

(B)

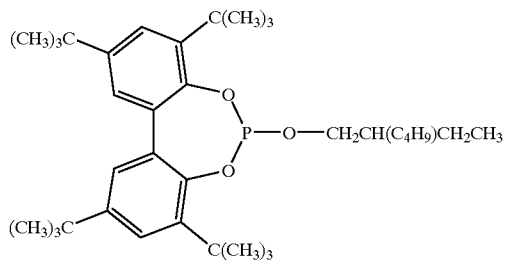

(C)

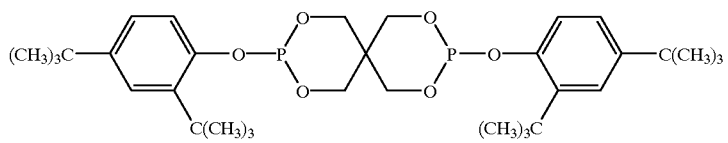

(D)

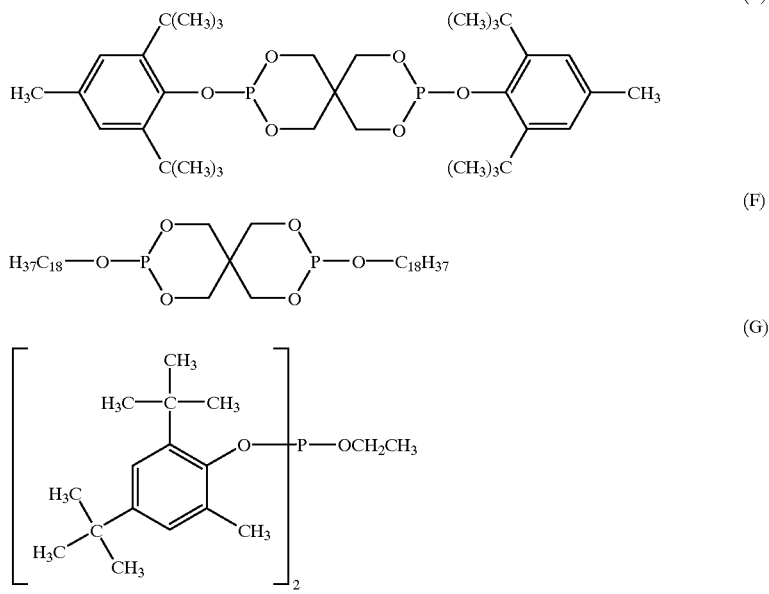

5. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example, N-benzyl-alpha-phenyl-nitrone, N-ethyl-alpha-methyl-nitrone, N-octyl-alpha-heptyl-nitrone, N-lauryl-alpha-undecyl-nitrone, N-tetradecyl-alpha-tridcyl-nitrone, N-hexadecyl-alpha-pentadecyl-nitrone, N-octadecyl-alpha-heptadecyl-nitrone, N-hexadecyl-alpha-heptadecyl-nitrone, N-ocatadecyl-alpha-pentadecyl-nitrone, N-heptadecyl-alpha-heptadecyl-nitrone, N-octadecyl-alpha-hexadecyl-nitrone, nitrone derived from N,N-dialkylhydroxylamine derived from hydrogenated tallow amine.

7. Thiosynergists, for example, dilauryl thiodipropionate or distearyl thiodipropionate.

8. Peroxide scavengers, for example esters of p-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

9. Polyamide stabilisers, for example, copper salts in combination with iodides and/or phosphorus compounds and salts of divalent manganese.

10. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or zink pyrocatecholate.

11. Nucleating agents, for example, inorganic substances such as talcum, metal oxides such as titanium dioxide or magnesium oxide, phosphates, carbonates or sulfates of, preferably, alkaline earth metals; organic compounds such as mono- or polycarboxylic acids and the salts thereof, e.g. 4-tert-butylbenzoic acid, adipic acid, diphenylacetic acid, sodium succinate or sodium benzoate; polymeric compounds such as ionic copolymers (ionomers).

12. Fillers and reinforcing agents, for example, calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

13. Other additives, for example, plasticisers, lubricants, emulsifiers, pigments, rheology additives, catalysts, flow-control agents, optical brighteners, flameproofing agents, antistatic agents and blowing agents.

14. Benzofuranones and indolinones, for example those disclosed in U.S. Pat. No. 4,325,863; U.S. Pat. No. 4,338,244; U.S. Pat. No. 5,175,312; U.S. Pat. No. 5,216,052; U.S. Pat. No. 5,252,643; DE-A-4316611; DE-A-4316622; DE-A-4316876; EP-A-0589839 or EP-A-0591102 or 3-[4-(2-acetoxyethoxy)phenyl]-5,7-di-tert-butyl-benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one, 3-(3,4-dimethylphenyl)-5,7-di-tert-butyl-benzofuran-2-one, 3-(2,3-dimethylphenyl)-5,7-di-tert-butyl-benzofuran-2-one.

The nature and amount of the further stabilizers added are determined by the nature of the substrate to be stabilized and by its intended use. It is common to employ 0.1–10, for example 0.2–5% by weight, based on the material to be stabilized.

It is particularly advantageous to employ the novel compounds in combination with sterically hindered amines, for example 2,2,6,6-tetraalkylpiperidine derivatives. The invention therefore embraces a synergistic stabilizer mixture comprising (a) a compound of the formula I and (b) at least one sterically hindered amine, its salt with any desired acid or its complex with a metal, and also embraces a composition comprising A) an organic material which is sensitive to oxidative, thermal and/or actinic breakdown/buildup, B) at least one compound of the formula I, and C) a conventional additive of the type of the sterically hindered amines.

Preferred sterically hindered amines are, for example, those indicated in the list above under 2.6 or those indicated below as additives to the novel coating compositions.

Of particular interest is the use of the compounds of the formula I as stabilizers in synthetic organic polymers, and corresponding compositions.

The organic materials to be protected are preferably natural, semisynthetic or synthetic organic materials. When using cosmetic preparations, the organic material to be protected is usually human or animal skin or hair.

The novel stabilizer mixtures can be employed with particular advantage in compositions which comprise as component A a synthetic organic polymer, especially a thermoplastic polymer, a binder for coatings such as, for example, paints, or a photographic material. Examples of suitable thermoplastic polymers are polyolefins, especially polyethylene (PE) and polypropylene (PP), and polymers containing heteroatoms in the main chain.

Examples of such polymers are the following classes of thermoplastic polymers:

1. Polyacetals, such as polyoxymethylene, and those polyoxymethylenes which contain comonomers such as ethylene oxide; polyacetals which are modified with thermoplastic polyurethanes, acrylates or MBS.

2. Polyphenylene oxides and sulfides and their mixtures with styrene polymers or polyamides.

3. Polyamides and copolyamides, for example those derived from diamines and dicarboxylic acids and/or from amino carboxylic acids or the corresponding lactams, such as polyamide 4, polyamide 6, polyamide 6/6, 6/10, 6/9, 6/12, 4/6, polyamide 11, polyamide 12, aromatic polyamides based on m-xylene, diamine and adipic acid; polyamides prepared from hexamethylenediamine and iso- and/or terephthalic acid with or without an elastomer as modifier, for example poly-2,4,4-trimethylhexamethyleneterephthalamide, poly-m-phenylene isophthalamide. Block copolymers of the abovementioned polyamides with polyolefins, olefin copolymers, ionomers or chemically bonded or grafted elastomers; or with polyethers, for example with polyethylene glycol, polypropylene glycol or polytetramethylene glycol. Furthermore, copolyamides or polyamides modified with EPDM or ABS; and polyamides which are condensed during processing (RIM polyamide systems).

4. Polyureas, polyimides, polyamideimides and polybenzimidazoles.

5. Polyesters, for example those derived from dicarboxylic acids and dialcohols and/or from hydroxy carboxylic acids or the corresponding lactones, such as polyethylene terephthalate, polybutylene terephthalate, poly-1,4-dimethylol-cyclohexane terephthalate, polyhydroxybenzoates, and also block polyether-esters derived from polyethers having hydroxyl end groups; and also polyesters modified with polycarbonates or MBS.

6. Polycarbonates and polyestercarbonates, especially aromatic polycarbonates, for example those based on 2,2-bis(4-hydroxyphenyl)propane or 1,1-bis(4-hydroxyphenyl)cyclohexane.

7. Polysulfones, polyether sulfones and polyether ketones, especially aromatic polymers from this class.

8. Mixtures (polyblends) of such polymers with one another or with other polymers, for example with polyolefins, polyacrylates, polydienes or other elastomers as impact modifiers.

Among these, preference is given to the polycarbonates, polyesters, polyamides, polyacetals, polyphenylene oxides and polyphenylene sulfides, but especially to the polycarbonates. Polycarbonates are to be understood as meaning, in particular, those polymers whose constitutional repeating unit is of the formula —[O—A—O—CO]—, in which A is a divalent phenolic radical. Examples of A are given, inter alia, in U.S. Pat. No. 4,960,863 and in DE-A-39 22 496.

The polymers of component (A) can be linear or branched. The shaping of these polymers takes place at a relatively high temperature; polycarbonate, for example, is injection molded at 220–330° C. At these temperatures the majority of the customary light stabilizers and antioxidants are unstable and begin to break down. The abovementioned mixtures, however, are extremely temperature-stable and are therefore particularly suitable for stabilizing the polymers mentioned.

Use in multicoat systems is also of interest. In this case a novel polymer composition having a relatively high content of novel stabilizer, for example 5–15% by weight, is applied in a thin coat (10–100 $\mu$m) to a shaped article comprising a polymer which contains little or no stabilizer of the formula I. Application can take place at the same time as the shaping of the base structure, for example by coextrusion. Application can also be made, however, to the ready-shaped base structure, for example by lamination with a film or by coating with a solution. The outer coat or coats of the finished article have the function of a UV filter which protects the interior of the article against UV light. The outer coat contains preferably 5–15% by weight, in particular 5–10% by weight, of at least one compound of the formula I. The polymers stabilized in this way are notable for high weathering stability, and especially by high resistance to UV light. As a result, even when used outdoors, they retain their mechanical properties and their colour and their gloss over a long period.

Likewise particularly preferred organic materials are coating compositions and photographic material.

The invention therefore preferably also provides a composition in which the novel compound is incorporated in a thermoplastic polymer, a film-forming binder, especially one based on acrylic, alkyd, polyurethane, polyester or polyamide resin or appropriately modified resins, a photographic material or a cosmetic preparation, including a cosmetic hair preparation, for example a cosmetic or a suncream. The material to be protected (component A) can in this case be, for example, a thermoplastic polymer, a film-forming binder, especially one based on acrylic, alkyd, polyurethane, polyester or polyamide resin or appropriately modified resins, a photographic material, or human or animal skin or hair.

The use of the novel compounds as stabilizers for coatings, for example for paints, is of particular interest. The invention also therefore provides those compositions whose component A is a film-forming binder.

The novel coating composition contains preferably 0.01–10 parts by weight, especially 0.05–10 parts by weight and, in particular, 0.1–5 parts by weight of the novel stabilizer B per 100 parts by weight of solid binder A.

Multicoat systems are also possible here, in which the concentration of the compound of the formula I (component B) in the top layer can be higher, for example from 1 to 15 parts by weight, especially 3–10 parts by weight of B per 100 parts by weight of solid binder A.

The use of the compound of the formula I as a stabilizer in coatings brings with it the additional advantage that delamination, i.e. the flaking of the coating from the substrate, is prevented. This advantage is particularly manifest in the case of metallic substrates, even in the case of multicoat systems on metallic substrates.

Suitable binders (component A) are in principle all those which are customary in the art, for example those described in Ullmann's Encyclopedia of Industrial Chemistry, 5th ed., Vol. A18, pp. 368–426, VCH, Weinheim 1991. The binder is generally a film-forming binder based on a thermoplastic or thermosetting resin, predominantly on a thermosetting resin. Examples thereof are alkyd, acrylic, polyester, phenolic, melamine, epoxy and polyurethane resins and mixtures thereof.

Component A can be a cold-curable or a heat-curable binder, the addition of a curing catalyst possibly being advantageous. Examples of suitable catalysts which accelerate the curing of the binder are described in Ullmann's Encyclopedia of Industrial Chemistry, Vol. A18, p.469, VCH Verlagsgesellschaft, Weinheim 1991.

Preference is given to coating compositions in which component A is a binder comprising a functional acrylate resin and a crosslinker.

Examples of coating compositions with specific binders are:

1. Paints based on cold- or heat-crosslinkable alkyd, acrylate, polyester, epoxy or melamine resins or mixtures of such resins, with or without addition of a curing catalyst;
2. two-component polyurethane paints based on hydroxyl-containing acrylate, polyester or polyether resins and on aliphatic or aromatic isocyanates, isocyanurates or polyisocyanates;
3. one-component polyurethane paints based on blocked isocyanates, isocyanurates or polyisocyanates which are deblocked in the course of stoving;
4. one-component polyurethane paints based on aliphatic or aromatic urethanes or polyurethanes and on hydroxyl-containing acrylate, polyester or polyether resins;
5. one-component polyurethane paints based on aliphatic or aromatic urethane acrylates or polyurethane acrylates having free amine groups in the urethane structure and on melamine resins or polyether resins, with or without addition of a curing catalyst;
6. two-component paints based on (poly)ketimines and on aliphatic or aromatic isocyanates, isocyanurates or polyisocyanates;
7. two-component paints based on (poly)ketimines and on an unsaturated acrylate resin or a polyacetoacetate resin or a methacrylamidoglycolate methyl ester;
8. two-component paints based on carboxyl- or amino-containing polyacrylates and polyepoxides;
9. two-component paints based on acrylate resins containing anhydride groups and on a polyhydroxy or polyamino component;
10. two-component paints based on acrylate-containing anhydrides and polyepoxides;
11. two-component paints based on (poly)oxazolines and on acrylate resins containing anhydride groups, or unsaturated acrylate resins or aliphatic or aromatic isocyanates, isocyanurates or polyisocyanates;
12. two-component paints based on unsaturated polyacrylates and polymalonates;
13. thermoplastic polyacrylate paints based on thermoplastic acrylate resins or externally crosslinking acrylate resins in combination with etherified melamine resins;
14. paint systems based on siloxane-modified or fluorine-modified acrylate resins.

The novel coating composition preferably comprises, in addition to components A and B, as component C a light stabilizer of the sterically hindered amine, 2-(2-hydroxyphenyl)-1,3,5-triazine and/or 2-hydroxyphenyl-2H-benzotriazole type, for example as set out in the above list under sections 2.1, 2.6 and 2.8. Of particular technical interest in this context is the addition of 2-monoresorcinyl-4,6-diaryl-1,3,5-triazines and/or 2-hydroxyphenyl-2H-benzotriazoles.

In order to achieve maximum light stability it is particularly advantageous to add sterically hindered amines, as set out in the above list under 2.6. The invention therefore also provides a coating composition which in addition to components A and B comprises as component C a light stabilizer of the sterically hindered amine type.

This stabilizer is preferably a 2,2,6,6-tetraalkylpiperidine derivative which comprises at least one group of the formula

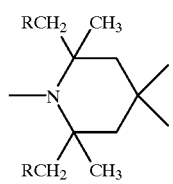

in which R is hydrogen or methyl, especially hydrogen.

Component C is preferably used in an amount of 0.05–5 parts by weight per 100 parts by weight of the solid binder. Examples of tetraalkylpiperidine derivatives which can be used as component C are given in EP-A-356 677, pages 3–17, sections a) to f). These sections of this EP-A are considered as part of the present description. It is particularly judicious to employ the following tetraalkylpiperidine derivatives:

bis-(2,2,6,6-tetramethylpiperidin-4-yl) succinate,
bis-(2,2,6,6-tetramethylpiperidin-4-yl) sebacate,
bis-(1,2,2,6,6-pentamethylpiperidin-4-yl) sebacate,
di(1,2,2,6,6-pentamethylpiperidin-4-yl) butyl(3,5-di-tert-butyl-4-hydroxy-benzyl)malonate,
bis-(1-octyloxy-2,2,6,6-tetramethylpiperidin-4-yl) sebacate,
tetra(2,2,6,6-tetramethylpiperidin-4-yl) butane-1,2,3,4-tetracarboxylate,
tetra(1,2,2,6,6-pentamethylpiperidin-4-yl) butane-1,2,3,4-tetracarboxylate,
2,2,4,4-tetramethyl-7-oxa-3,20-diaza-21-oxodispiro [5.1.11.2]heneicosane,
8-acetyl-3-dodecyl-1,3,8-triaza-7,7,9,9-tetramethylspiro [4.5]decane-2,4-dione,
1,1-bis(1,2,2,6,6-pentamethylpiperidin-4-yl-oxycarbonyl)-2-(4-methoxyphenyl)-ethene, or a compound of the formulae

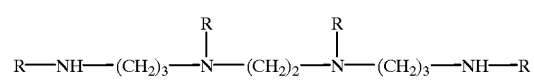

-continued

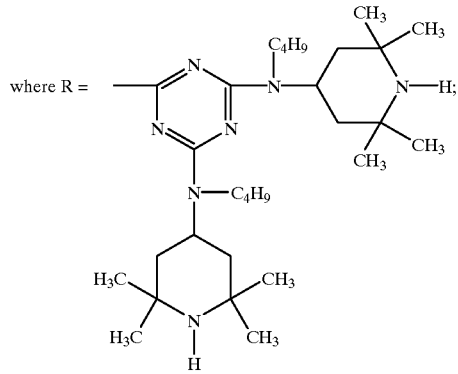

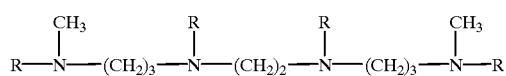

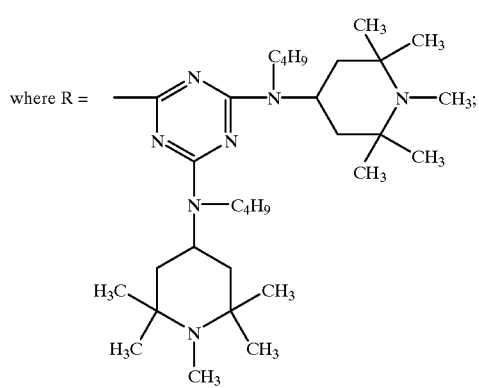

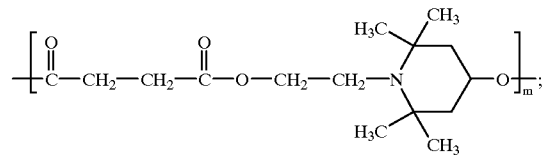

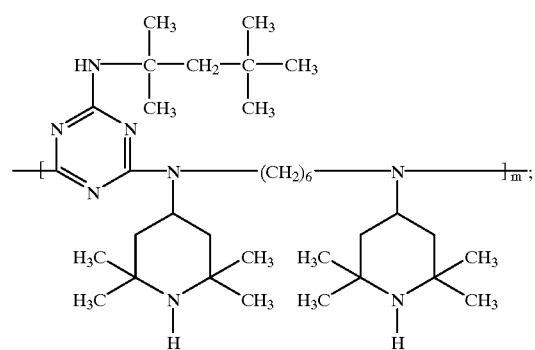

-continued

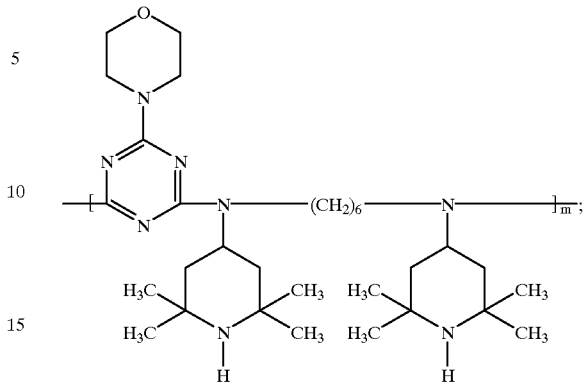

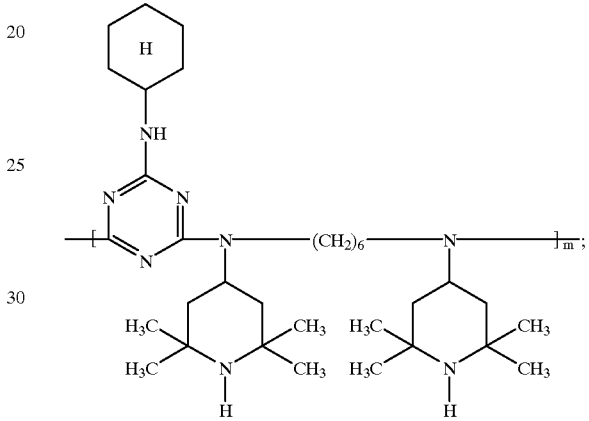

or

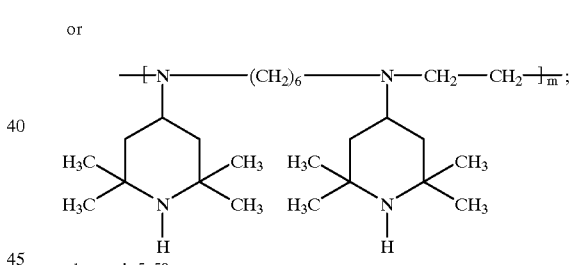

where m is 5–50.

where m is 5–50.

In addition to components A, B and, if present, C, the coating composition may also comprise further components, for example solvents, pigments, dyes, plasticizers, stabilizers, thixotropic agents, drying catalysts and/or levelling assistants.

Examples of possible components are those as described in Ullmann's Encyclopedia of Industrial Chemistry, 5th ed., Vol. A18, pp. 429–471, VCH, Weinheim 1991.

Possible drying catalysts or curing catalysts are, for example, organometallic compounds, amines, amino-containing resins and/or phosphines. Examples of organometallic compounds are metal carboxylates, especially those of the metals Pb, Mn, Co, Zn, Zr or Cu, or metal chelates, especially those of metals Al, Ti or Zr, or organometallic compounds such as organotin compounds, for example.

Examples of metal carboxylates are the stearates of Pb, Mn or Zn, the octoates of Co, Zn or Cu, the naphthenates of Mn and Co or the corresponding linoleates, resinates or tallates. Examples of metal chelates are the aluminium, titanium or zirconium chelates of acetylacetone, ethyl acetylacetate, salicylaldehyde, salicylaldoxime, o-hydroxyacetophenone or ethyl trifluoroacetylacetate, and the alkoxides of these metals. Examples of organotin compounds are dibutyltin oxide, dibutyltin dilaurate or dibutyltin dioctoate. Examples of amines are, in particular, tertiary amines, for example tributylamine, triethanolamine, N-methyldiethanolamine, N-dimethylethanolamine, N-ethyl-morpholine, N-methylmorpholine or diazabicyclooctane (triethylenediamine) and their salts. Further examples are quaternary ammonium salts, for example trimethylbenzylammonium chloride. Amino-containing resins are simultaneously binder and curing catalyst. Examples thereof are amino-containing acrylate copolymers. Phosphines, for example triphenylphosphine, can also be used as curing catalyst.

The novel coating compositions can also be radiation-curable coating compositions. In this case the binder consists essentially of monomeric or oligomeric compounds having ethylenically unsaturated bonds (prepolymers), which after application are cured, i.e. converted into a crosslinked, high molecular mass form, by actinic radiation. Where the system is a UV-curing system, it generally also includes a photoinitiator. Appropriate systems are described in the abovementioned publication Ullmann's Encyclopedia of Industrial Chemistry, 5th ed., Vol. A18, pages 451–453. In radiation-curable coating compositions the novel stabilizers can be employed even without the addition of sterically hindered amines.

The novel coating compositions can be applied to any desired substrates, for example to metal, wood, plastic or ceramic materials. In the case of the finishing of automobiles they are preferably used as topcoat. If the topcoat consists of two layers of which the lower layer is pigmented and the upper layer is not, then the novel coating composition can be used for the upper or the lower layer or for both layers, but preferably for the upper layer.

The novel coating compositions can be applied to the substrates by the customary techniques, for example by spreading, spraying, flow coating, dipping or electrophoresis; see also Ullmann's Encyclopedia of Industrial Chemistry, 5th ed., Vol.A18, pp. 491–500.

Depending on the binder system the coating can be cured at room temperature or by heating. The coating is preferably cured at 50–150° C., powder coatings also at higher temperatures.

The coatings obtained in accordance with the invention possess an outstanding resistance to the damaging effects of light, oxygen and heat; particular mention should be made of the good light stability and weathering stability of the resulting coatings, for example paints.

The invention therefore also provides a coating, especially a paint, which is stabilized against the damaging effects of light, oxygen and heat by the addition of a compound of the formula I. The paint is preferably a topcoat for automobiles. The invention in addition comprises a process for stabilizing a coating based on organic polymers against damage by light, oxygen and/or heat, which comprises mixing with the coating composition a compound of the formula I, and provides for the use of compounds of the formula I in coating compositions as stabilizers against damage by light, oxygen and/or heat.

The coating compositions can comprise an organic solvent or solvent mixture in which the binder is soluble. The coating composition can also be an aqueous solution or dispersion, however. The vehicle can also be a mixture of an organic solvent and water. The coating composition may also be a high-solids system or can be solvent-free (for example powder coating). Powder coatings are those, for example, as described in Ullmann's Encyclopedia of Industrial Chemistry, 5th ed., A18, pages 438–444. The powder coating can also be in the form of a powder slurry, i.e. a dispersion of the powder in—preferably—water.

The pigments can be inorganic, organic or metallic pigments. The novel coating compositions preferably contain no pigments and are used as clearcoat.

Likewise preferred is the use of the coating composition as a topcoat for applications in the automotive industry, especially as a pigmented or unpigmented top layer of the coating system. Its use for underlying coats, however, is also possible.

The novel compounds of the formula I are also particularly suitable as UV filters for protecting the skin and the hair of humans and animals against the damaging action of UV radiation. These compounds are therefore suitable as light stabilizers in cosmetic, pharmaceutical and veterinary preparations. These compounds can be used either in solution or in the micronized state.

The invention therefore additionally provides a cosmetic preparation comprising at least one compound of the formula I and cosmetically compatible excipients or auxiliaries.

For cosmetic use the novel light stabilizers, unless dissolved, usually have a mean particle size in the range from 0.02 to 2, preferably 0.05 to 1.5, and, with very particular preference, from 0.1 to 1.0 $\mu$. The insoluble novel UV absorbers can be brought to the desired particle size by customary methods, for example grinding with, for example, a jet, ball, vibration or hammer mill. Grinding is preferably carried out in the presence of from 0.1 to 30, preferably from 0.5 to 15% by weight, based on the UV absorber, of a grinding assistant such as, for example, an alkylated vinylpyrrolidone polymer, a vinylpyrrolidone-vinyl acetate copolymer, an acylglutamate or, in particular, a phospholipid.

In addition to the novel UV absorbers, the cosmetic compositions may also include one or more other UV protection agents, for example triazines, oxanilides, triazoles or vinyl-containing amides or cinnamamides. Such protectants are described, for example, in GB-A-2,286,774 or else are known from Cosmetics & Toiletries (107), 50 ff (1992).

The novel cosmetic compositions contain from 0.1 to 25, for example from 0.1 to 15, especially from 0.5 to 10% by weight, based on the overall weight of the composition, of a UV absorber or a mixture of UV absorbers and a cosmetically compatible auxiliary.

The cosmetic compositions can be prepared by physical mixing of the UV absorber or absorbers with the auxiliary by customary methods, for example by simply stirring together the individual components.

The novel cosmetic compositions can be formulated as a water-in-oil or oil-in-water emulsion, as an oil-in-alcohol lotion, as a vesicular dispersion of an ionic or nonionic amphiphilic lipid, as a gel, as a solid stick or as an aerosol formulation. As a water-in-oil or oil-in-water emulsion the cosmetically compatible auxiliary contains preferably from 5 to 50% of an oil phase, from 5 to 20% of an emulsifier and from 30 to 90% of water. The oil phase in this case can be any oil suitable for cosmetic formulations, for example one or more hydrocarbon oils, a wax, a natural oil, a silicone oil, a fatty acid ester or a fatty alcohol. Preferred monools and polyols are ethanol, isopropanol, propylene glycol, hexylene glycol, glycerol and sorbitol.

Cosmetic hair compositions can be
in the form of a shampoo, a lotion, a gel or an emulsion for rinsing, before or after shampooing, before or after dyeing or bleaching, before or after a permanent wave or before or after a straightening operation,
in the form of a lotion, a mousse or a gel for styling or treatment,
in the form of a lotion or a gel for brushing or for waving,
in the form of a hair lacquer,
in the form of a composition for permanent waving or for straightening, for dyeing or bleaching the hair.

For example, the following cosmetic hair formulations can be used:

$a_1$) a spontaneously emulsifying stock formulation consisting of the UV absorber, PEG-6-$C_{10}$ oxo alcohol and sorbitan sesquioleate, to which water and any desired quaternary ammonium compound, for example 4% minkamidopropyl-dimethyl-2-hydroxyethylammonium chloride or quaternium 80 are added;

$a_2$) a spontaneously emulsifying stock formulation consisting of the UV absorber, tributyl citrate and PEG-20-sorbitan monooleate, to which water and any desired quaternary ammonium compound, for example 4% minkamidopropyl-dimethyl-2-hydroxyethylammonium chloride or quaternium 80 are added;

b) quat-doped solutions of the UV absorber in butyltriglycol and tributyl citrate;

c) dispersions of micronized UV absorbers, obtained by known methods (precipitation from solutions or mixed solutions, grinding), having a mean diameter of 0.05–1.0 mm in APG (e.g. Plantaren) and a quat (e.g. mink-amidopropyldimethyl-2-hydroxyethylammonium chloride) in an aqueous formulation;

d) mixtures or solutions of the UV absorber with n-alkylpyrrolidone.

The cosmetic compositions may also include further components, examples being emollients, emulsion stabilizers, skin moisteners, tanning accelerators, thickeners such as xanthan, moisture retention agents such as glycerol, preservatives, fragrances and colorants.

The novel cosmetic formulations feature excellent protection of the human skin and hair against the damaging influence of sunlight.

Other materials to be stabilized with the novel compositions are recording materials. By such materials are meant, for example, those described in Research Disclosure 1990, 31429 (pages 474–480) for photographic reproduction and other reprographic techniques.

The novel recording materials comprise, for example, those for pressure-sensitive copying systems, microcapsule photocopier systems, heat-sensitive copier systems, photographic material and ink-jet printing.

The novel recording materials feature an unexpectedly high quality, especially in terms of their light stability.

The novel recording materials have a structure which is known per se and which corresponds to the utility. They consist of a base, for example paper or plastic film, on which one or more coatings are applied. Depending on the type of material, these coats contain the suitable components required, in the case of photographic material for example silver halide emulsions, colour couplers, dyes and the like. The material intended especially for ink-jet printing has a customary base on which there is an absorption layer suitable for ink. Uncoated paper can likewise be employed for ink-jet printing; in this case, the paper functions simultaneously as a base and has the absorbent for the ink. Suitable material for ink-jet printing is described, inter alia, in U.S. Pat. No. 5,073,448, the disclosure content of which is regarded as part of the present description.

The recording material can also be transparent, for example in the case of projection films.

The compound or compounds of the formula I can be incorporated into the material even in the course of manufacture; in papermaking, for example, by addition to the pulp. Another method of use is the spraying of the material with an aqueous solution of compound(s) of the formula I, or the addition thereof to the coating. Coatings for transparent recording materials for projection must not contain any light-scattering particles such as pigments or fillers.

The colour-binding coatings can contain further additives, for example antioxidants, light stabilizers (including UV absorbers which are not included among the novel UV absorbers), viscosity improvers, brighteners, biocides and/or antistats.

The coating is usually prepared as follows: The water-soluble components, for example the binder, are dissolved in water and mixed. The solid components, for example fillers and other additives as already described, are dispersed in this aqueous medium. Dispersion is advantageously brought about with the aid of equipment such as ultrasonic devices, turbine agitators, homogenizers, colloid mills, bead mills, sand mills, high-speed stirrers and the like. A particular advantage of the compounds of the formula I is their ease of incorporation into the coating.

As mentioned, the novel recording materials cover a broad field of use. Compounds of the formula I can be employed, for example, in pressure-sensitive copier systems. They can be added to the paper to protect the microencapsulated dye precursors against light, or to the binder of the developer layer for protecting the dyes formed therein.

Photocopier systems with light-sensitive microcapsules which are developed by pressure are described, inter alia, in U.S. Pat. Nos. 4,416,966; 4,483,912; 4,352,200; 4,535,050; 4,5365,463; 4,551,407; 4,562,137 and 4,608,330; and also in EP-A-139,479; EP-A-162,664; EP-A-164,931; EP-A-237,024; EP-A-237,025 and EP-A-260,129. In all these systems the compounds of the formula I can be added to the colour-accepting layer. Alternatively, the compounds of the formula I can be added to the donor layer for protecting the colour formers against light.

The compounds of the formula I can also be employed in recording materials which are based on the principle of photopolymerization, photosoftening or the rupture of microcapsules, or when heat-sensitive or photosensitive diazonium salts, leuco dyes with oxidizing agent or colour lactones with Lewis acids are used.

Heat-sensitive recording material exploits the colour-imparting reaction between a colourless or weakly coloured base dye and an organic or inorganic colour developer, the recorded image being produced by heat-induced contact of the two materials. This type of heat-sensitive recording material is very widespread, not only as the recording medium for faxes, computers, etc., but also in many other fields, for example in label printing.

The heat-sensitive recording material according to the present invention is composed of a base, a heat-sensitive colour-forming recording layer on this base, and, optionally, a protective layer on the heat-sensitive, colour-forming recording layer. The heat-sensitive, colour-forming recording layer contains as its principal constituent a colour-imparting compound and a colour-developing compound, and also a compound of the formula (I). If the said protective layer is present, the compound of the formula (I) can also be incorporated into the protective layer.

Heat-sensitive recording materials are described, for example, in JP-A 8-267 915.

Further fields of use are recording materials for dye diffusion transfer printing, thermal wax transfer printing and dot matrix printing, and for use with electrostatic, electrographic, electrophoretic, magnetographic and laser-electrophotographic printers, recorders or plotters. Of the materials mentioned, preference is given to recording materials for dye diffusion transfer printing, as are described, for example, in EP-A-507,734.

Compounds of the formula I can also be employed in inks, preferably for ink-jet printing, for example those as described in U.S. Pat. No. 5,098,477, the disclosure content of which is regarded as part of the present description. The invention therefore also provides an ink comprising at least one compound of the formula I as stabilizer. The ink, especially for ink-jet printing, contains preferably water. Inks contain the stabilizer of the formula I usually in a concentration of from 0.01 to 20% by weight, in particular from 0.5 to 10% by weight.

The novel recording materials, for example photographic recording materials, also offer the advantage over materials comprising conventional UV absorbers that the UVAs of the formula (I) are required in a comparatively small amount, meaning also that the thickness of the UVA-containing layer remains low, a factor which has a positive effect, inter alia, on the imaging properties. Another advantage of the novel stabilizers is their heightened inherent stability under extreme climatic conditions, especially at high humidity and high temperature. The novel photographic material can be a black and white or a colour photographic material; colour photographic material is preferred.

Examples of colour photographic materials are colour negative films, colour reversal films, colour positive films, colour photographic paper, colour reversal photographic paper, colour-sensitive materials for the dye diffusion transfer process or the silver dye bleach process.

Examples of suitable bases for the production of colour photographic materials are films and sheets of semisynthetic and synthetic polymers, such as cellulose nitrate, cellulose acetate, cellulose butyrate, polystyrene, polyvinyl chloride, polyethylene terephthalate and polycarbonate, and paper laminated with a barytes layer or an α-olefin polymer layer (e.g. polyethylene). These bases can have been coloured with dyes or pigments, for example titanium dioxide. They can also have been coloured black for the purposes of light shielding. The surface of the base is generally subjected to a treatment for improving the adhesion of the photographic emulsion layer, for example corona discharge with subsequent application of a substrate layer.

The novel material preferably comprises the silver halide emulsion layers starting from the base, in the sequence blue-sensitive, green-sensitive and red-sensitive layer. In the novel colour photographic material the UV absorber is preferably in a layer above the green-sensitive layer, particularly preferably in a layer above the silver halide emulsion layer(s).

The novel UV absorber is preferably present in the photographic material in an amount of from 0.001 to 10 g per m², for example from 0.1 to 8 g/m², especially from 0.005 to 6 and, in particular, from 0.01 to 4 g/m².

The novel colour photographic recording material is preferably a material having the following layer sequence:

| | |
|---|---|
| a | a: Protective layer |
| b | b: Interlayer (may be absent) |
| c | c: Red-sensitive layer |
| d | d: Interlayer |
| e | e: Green-sensitive layer |
| f | f: Interlayer |
| g | g: Blue-sensitive layer |
| h | h: Base |

Another example is a material having a similar layer structure but in which layer a is absent. The novel UV absorber of the formula (I), in the layer sequence depicted, is present judiciously, for example, in at least one of layers a–e, preferably in layer a, b, c and/or d, especially in a, b and/or c, and in particular in a and/or b.

Preference is generally given to a photographic recording material comprising a compound of the formula (I) in a layer above the silver halide emulsion layer(s). Preference is also given to photographic recording material comprising at least one each of a red-sensitive and green-sensitive silver halide emulsion layer and, in between them, an interlayer, where at least one compound of the formula (I) is present in the interlayer between the red-sensitive and the green-sensitive silver halide emulsion layer. Very particularly preferred photographic recording material comprises at least one each of a red-sensitive, a green-sensitive and a blue-sensitive silver halide emulsion layer and also at least two interlayers between the aforementioned layers and a protective layer, where at least one compound of the formula (I) is present in at least one layer above the green-sensitive silver halide emulsion layer, and the silver halide emulsion layers contain dark-storage stabilizers and/or light stabilizers.

Essential constituents of the colour-photographic emulsion layers are binders, silver halide particles and colour couplers.

Of especial interest, for example, is a colour photographic recording material comprising, on a base, at least one blue-sensitive silver halide emulsion layer containing at least one yellow coupler, at least one green-sensitive silver halide emulsion layer containing at least one magenta coupler, at least one red-sensitive silver halide emulsion layer containing at least one cyan coupler, and customary top layer(s) and interlayer(s), at least one of the layers comprising a compound of the formula (I).

The photographic emulsions can be spectrally sensitized using methine dyes or other dyes. Particularly suitable dyes are cyanine dyes and merocyanine dyes, including complex merocyanine dyes.

An overview of the polymethine dyes which are suitable as spectral sensitizers, their appropriate combinations and supersensitizing combinations is given in Research Disclosure 17643 (Dec. 1978), Chapter IV.

The differently sensitized emulsion layers are allocated non-diffusing monomeric or polymeric colour couplers, which may be located in the same layer or in an adjacent layer. It is common to assign cyan couplers to the red-sensitive layers, magenta couplers to the green-sensitive layers and yellow couplers to the blue-sensitive layers.

Yellow couplers which can be used in the novel material are preferably compounds of the formula A

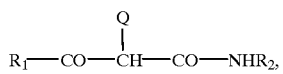
(A)

in which $R_1$ is alkyl, cycloalkyl, arylamino, aniline, a heterocyclic group or aryl, $R_2$ is aryl and Q is hydrogen or a group which can be eliminated by reaction with the oxidized developer.

Magenta couplers can, for example, be simple 1-aryl-5-pyrazolones, or pyrazole derivatives fused with 5-membered hetero-rings, for example imidazopyrazoles, pyrazolopyrazoles, pyrazolotriazoles or pyrazolotetrazoles.

Cyan couplers can, for example, be derivatives of phenol, 1-naphthol, pyrazoloazole, pyrroloazole or of pyrazoloquinazolone. One group of cyan couplers is of the formula E

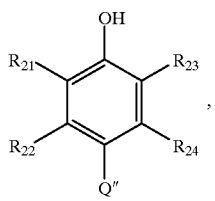
(E)

in which $R_{21}$, $R_{22}$, $R_{23}$ and $R_{24}$ are hydrogen, halogen, alkyl, carbamoyl, amino, sulfonamido, phosphoramido or ureido. $R_{21}$ is preferably H or Cl, $R_{22}$ is preferably an alkyl or amino group. $R_{23}$ is preferably an amino group and $R_{24}$ is preferably hydrogen. Q" is hydrogen (4-equivalent coupler) or a leaving group (2-equivalent coupler) which is eliminated on reaction with the oxidized developer. An exhaustive listing of cyan couplers can be found in U.S. Pat. No. 4,456,681.

The cyan couplers employed in the red-sensitive silver halide emulsion layer of the novel material are preferably of the formula

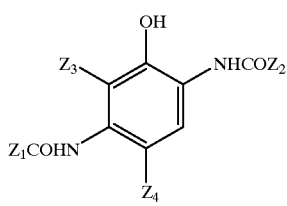
(E-12)

and/or of the formula

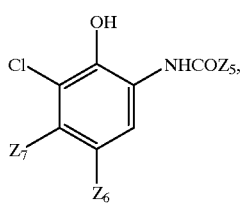
(E-13)

in which $Z_1$ is alkyl, aryl, $Z_2$ is alkyl, cycloalkyl, aryl, a heterocyclic group or a ballast group, $Z_3$ is hydrogen or halogen, $Z_1$ and $Z_3$ together can form a ring, and $Z_4$ is hydrogen or a leaving group, and $Z_5$ is a ballast group, $Z_6$ is hydrogen or a leaving group and $Z_7$ is alkyl; and also those of the formulae E20 and/or E21

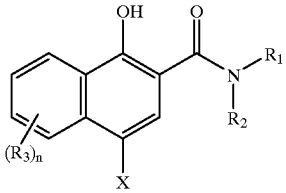
(E-20)

in which $R_1$ is preferably substituted phenyl and $R_2$ and $R_3$ are preferably H and X is preferably H or a group which is cleaved by reaction with the oxidized form of the developer, and

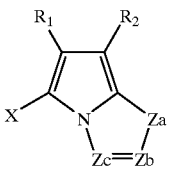
(E-21)

in which Za is —NH— or —CH($R_3$)—; Zb and Zc independently of one another are —C($R_4$)= or —N=; $R_1$, $R_2$ and $R_3$ are each an electron-attracting group having a Hammett substituent constant $\sigma_p$ of at least 0.2, with the sum of the $\sigma_p$ values of $R_1$ and $R_2$ being at least 0.65; $R_4$ is H or a substituent, and if two $R_4$s are present in the formula, they can be identical or different; and X is H or a group capable of elimination in the coupling reaction with the oxidation product of an aromatic primary amine as colour developer; or $R_1$, $R_2$, $R_3$, $R_4$ or X is a divalent group by means of which the cyan coupler is able to form a dimer or higher polymer, or to react with a polymer chain to form a homo- or copolymer.

Preference is given to a photographic material in which the red-sensitive silver halide emulsion layer comprises a cyan coupler of one of the formulae C1, C2, C3, C4, C5, C6, C7 and C8

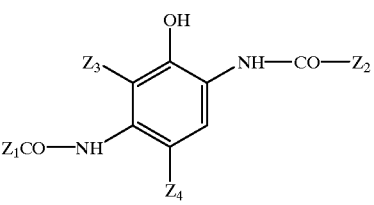
C1

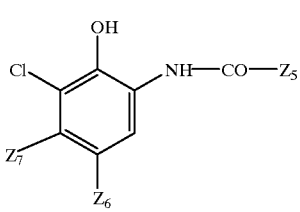
C2

-continued

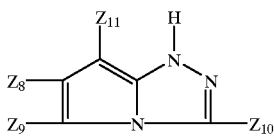
C3

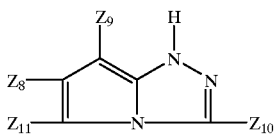
C4

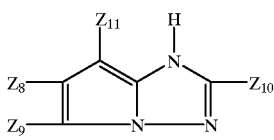
C5

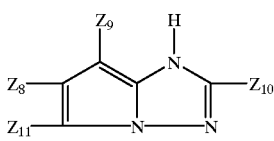
C6

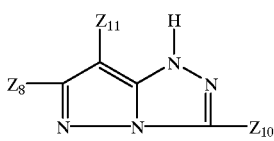
C7

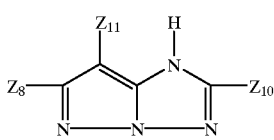
C8 in which
$Z_1$ is alkyl or aryl,
$Z_2$ is alkyl, cycloalkyl, aryl, a heterocyclic group or a ballast group,
$Z_3$ is H or halogen, or $Z_1$ and $Z_3$ together form a ring,
$Z_4$ is H or a leaving group,
$Z_5$ is a ballast group,
$Z_6$ is H or a leaving group,
$Z_7$ is alkyl,
$Z_8$ and $Z_9$ independently of one another are H or a substituent, at least one of the groups $Z_8$ and $Z_9$ being an electron-withdrawing group having a Hammett constant $(-\sigma_p)$ of 0.15 or more [$Z_8$ and $Z_9$ can be connected to one another to form a ring structure];
$Z_{10}$ is a substituent and
$Z_{11}$ is H or a leaving group.

The cyan couplers can also be connected to one another by way of the radicals $Z_8$, $Z_9$, $Z_{10}$ or $Z_{11}$ to form dimers or polymers.

Suitable leaving groups are in general those substituents which are set free after coupling with the oxidation product of a colour developer based on aromatic primary amines.

The novel photographic material preferably comprises those cyan couplers of the formulae $C_1$–$C_8$ in which
$Z_1$ is alkyl or aryl,
$Z_2$ is alkyl, aryl, or a ballast group,
$Z_3$ is H or halogen,
$Z_4$ is H or a leaving group,
$Z_5$ is a ballast group,
$Z_6$ is H or a leaving group,
$Z_7$ is alkyl,
$Z_8$ and $Z_9$ independently of one another are CN, $CF_3$, $COOZ_{12}$, $COZ_{12}$, $SO_2Z_{12}$, $CON(Z_{13})Z_{14}$, $SO_2N(Z_{13})Z_{14}$, and
$Z_{12}$ is unsubstituted alkyl or aryl,
$Z_{13}$ and $Z_{14}$ independently of one another are unsubstituted or substituted alkyl, aryl, heterocyclyl, alkoxy, aryloxy or heterocyclyloxy, and
$Z_{13}$ can also be H;
$Z_{10}$ embraces the definitions given for $Z_8$ and $Z_9$ or is alkyl, aryl, heterocyclyl, nitro, NH—CO—$Z_{15}$, $N(Z_{15})Z_{16}$, NH—CO—N($Z_{15}$)$Z_{16}$, NH—SO$_2$N($Z_{15}$), S—$Z_{15}$, NH—CO—O$Z_{15}$, NH—SO$_2$N($Z_{15}$)$Z_{16}$, SO$Z_{15}$, and
$Z_{15}$ and $Z_{16}$ are each a substituent, and $Z_{16}$ can also be H.

The photographic layers in the novel material, especially the layers b, c and/or d in the colour photographic material described above by way of example, can preferably include further UV absorbers. Examples of such UV absorbers are benzotriazoles, 2-hydroxybenzophenones, oxanilides, cyanoacrylates, salicylic esters, acrylonitrile derivatives or thiazolines, and also conventional 2-hydroxyphenyltriazines.

Such UV absorbers are described in more detail, for example, in the following publications: U.S. Pat. Nos. 3,314,794, 3,352,681, 3,705,805, 3,707,375, 4,045,229, 3,700,455, 3,700,458, 3,533,794, 3,698,907, 3,705,805, 3,738,837, 3,762,272, 4,163,671, 4,195,999, 4,309,500, 4,431,726, 4,443,543, 4,576,908, 4,749,643, 5,500,332, 5,455,152, GB-A-1,564,089, GB-A-2,293,608, EP-A-190, 003, -747755, -717313 and JP-A-71/2784, 81/111,826, 81/27,146, 88/53,543, 88155,542 and 96/69087. Preferred UV absorbers are benzotriazoles, especially 2-(2-hydroxyphenyl)benzotriazoles.

Preference is also given to photographic recording material comprising in addition a UV absorber, not of the formula (I), from the series of the 2-hydroxyphenyltriazines, as are described, for example, in U.S. Pat. No. 5,300,414, U.S. Pat. No. 5,489,503, U.S. Pat. No. 5,480,108, U.S. Pat. No. 4,826,978, EP-A-706083, JP-A han 08-267915 and U.S. Pat. No. 5,364,749.

The amount of the additional UV absorber or absorbers added is judiciously within the same range as indicated above for the novel UV absorbers.

Examples of particularly suitable compounds are: 2-Hydroxyphenyltriazines of the formula

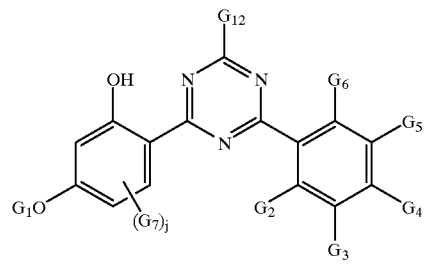

in which j is 0, 1, 2 or 3;
$G_1$ is alkyl, alkenyl or cycloalkyl;
$G_2$ and $G_6$ independently of one another are H, OH, halogen, alkyl, halomethyl, for example $CF_3$;
$G_3$, $G_5$ and $G_7$ independently of one another are H, OH, $OG_1$, halogen, alkyl, halomethyl, for example $CF_3$;
$G_4$ is H, OH, $OG_1$, halogen, alkyl, phenyl, halomethyl, for example $CF_3$, or alkenyl; and
$G_{12}$ is alkyl, phenylalkyl, cycloalkyl, $OG_1$, or in particular, a group of the formula

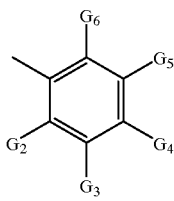

Alkyl or alkenyl substituents, or substituents which are aromatic or aliphatic ring systems, usually contain—within the context of the stated definitions—from 1 to 50 carbon atoms and can be interrupted one or more times by O, S, NR', SO$_2$, CO, phenylene, cyclohexylene, COO, OCO, —(SiR$_p$R$_q$O)— and/or substituted one or more times by OH, OR', NR'R'', halogen, —CN, alkenyl, phenyl, —SiR$_p$R$_q$R$_r$ or COOH, where R' and R'' independently of one another are H, alkyl, alkenyl or acyl, and R$_p$, R$_q$ and R$_r$ independently of one another are H, alkyl, alkenyl, phenyl, alkoxy, acyl or acyloxy. The abovementioned groups can also carry other substituents as well. Dimers or polymers are also possible.

Preferred 2-hydroxyphenyltriazines of this class are, for example, those of the formula

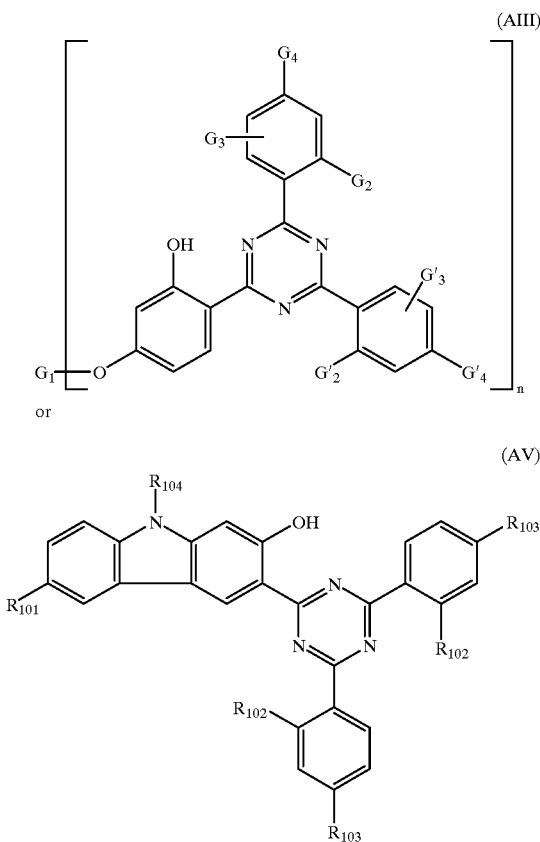

where, in formula AIII n is 1 or 2 and

G$_1$, if n=1, is alkyl which is uninterrupted and unsubstituted or is interrupted by one or more O and/or substituted by one or more of the radicals OH, glycidyloxy, alkenoxy, COOH, COOR$^e$, O—CO—R$^f$, or is alkenyl, cycloalkyl, unsubstituted or OH—, Cl— or CH$_3$-substituted phenylalkyl; or COR$^g$; SO$_2$—Rh; CH$_2$CH(OH)—R$^j$; where R$^e$ is alkyl; alkenyl; hydroxyalkyl; alkyl or hydroxyalkyl interrupted by one or more O; cycloalkyl; benzyl; alkylphenyl; phenyl; phenylalkyl; furfuryl; or CH$_2$CH(OH)—R$^j$;

R$^f$, R$^g$ independently of one another are alkyl, alkenyl or phenyl;

R$^h$ is alkyl, aryl or alkylaryl;

R$^j$ is aralkyl or CH$_2$OR$^k$;

R$^k$ is cyclohexyl, phenyl, tolyl or benzyl; and

G$_1$, if n=2, is alkylene; alkenylene; xylylene; alkylene or hydroxyalkylene interrupted by one or more O; hydroxyalkylene;

G$_2$ and G'$_2$ independently of one another are H, alkyl or OH;

G$_4$ and G'$_4$ independently of one another are H, alkyl, OH, alkoxy, halogen, and, if n=1, OG$_1$;

G$_3$ and G'$_3$ independently of one another are H, alkyl or halogen; and where, in formula A V, R$_{101}$ is H, C$_1$–C$_8$alkyl, C$_1$–C$_8$alkoxy;

R$_{102}$ and R$_{103}$ independently of one another are H, halogen, OH, C$_1$–C$_8$alkyl, C$_1$–C$_8$alkoxy;

R$_{104}$ is H, OH, C$_1$–C$_8$alkyl; C$_1$–C$_8$alkoxy.

Within the scope of the stated definitions G$_1$, G$_2$, G'$_2$, G$_3$, G'$_3$, G$_4$ and G'$_4$ may also carry additional substituents, for example an ethylenically unsaturated, polymerizable group. Dimers or polymers are also possible.

Particular preference is given to colour photographic materials in accordance with the present invention, in which at least one of the layers comprises a UV absorber of the formula A III in which n is 1;

G$_1$ is C$_1$–C$_{12}$alkyl which is unsubstituted or substituted by OH or COOR$^e$; or is C$_2$–C$_{12}$alkyl or C$_3$–C$_{15}$hydroxyalkyl, interrupted by one or more O; or is C$_3$–C$_6$alkenyl; cyclohexyl; C$_7$–C$_{11}$phenylalkyl; CH$_2$CH(OH)—R$^j$; where R$^e$ is C$_1$–C$_{18}$alkyl; C$_3$–C$_7$alkenyl; alkyl or hydroxyalkyl interrupted by one or more O;

R$^j$ is C$_7$–C$_{12}$aralkyl or CH$_2$OR$^k$;

R$^k$ is cyclohexyl, phenyl, tolyl or benzyl; and

G$_2$ and G'$_2$ are OH;

G$_4$ and G'$_4$ are OG$_1$;

G$_3$ and G'$_3$ independently of one another are H or methyl; especially those in which n is 1;

G$_1$ is C$_1$–C$_{12}$alkyl which is unsubstituted or substituted by COOR$^e$; or is C$_3$–C$_{15}$hydroxyalkyl which is interrupted by O; or is allyl, cyclohexyl or benzyl; where R$^e$ is C$_1$–C$_{12}$alkyl; allyl; C$_3$–C$_{12}$alkyl which is interrupted by one or more O;

G$_2$ and G'$_2$ are OH;

G$_4$ and G'$_4$ are OG$_1$;

G$_3$ and G'$_3$ are H.

Examples of such compounds include 2,4,6-tris(2-hydroxy-4-octyloxyphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2-hydroxy-3-butyloxypropyloxy)phenyl]-4,6-bis(2,4-dimethylphenyl)-1,3,5-triazine, 2-[2-hydroxy-4-(2-hydroxy-3-octyloxypropyloxy)phenyl]-4,6-bis(2,4-dimethylphenyl)-1,3,5-triazine, 2-[2-hydroxy-4-(2-hydroxy-3-tridecyloxypropyioxy)phenyl]-4,6-bis(2,4-dimethylphenyl)-1,3,5-triazine; and compounds of the following formulae:

Type (HPT-I)

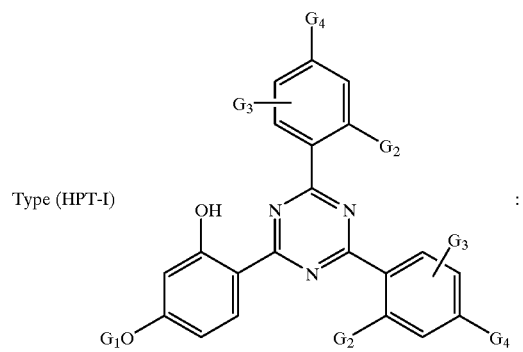

| No. | $G_1$ | $G_2$ | $G_4$ | $G_3$ |
|---|---|---|---|---|
| HPT-1 | $CH_2CH(OH)CH_2O-CO-C(CH_3)=CH_2$ | $CH_3$ | $CH_3$ | H |
| HPT-2 | $CH_2CH(OH)CH_2OC_{12}H_{25}/C_{13}H_{27}$(mixture) | $CH_3$ | $CH_3$ | H |
| HPT-3 | $CH_2CH(OH)CH_2O-C_4H_9(n)$ | $CH_3$ | $CH_3$ | H |
| HPT-4 | $CH_2COO-C_{18}H_{37}$ | H | H | m-$CF_3$ |
| HPT-5 | $C_8H_{17}$ | $CH_3$ | $CH_3$ | H |
| HPT-6 | $CH_2CH(OH)CH(C_2H_5)-C_4H_9(n)$ | $CH_3$ | $CH_3$ | H |
| HPT-6a | H | $CH_3$ | $CH_3$ | H |
| HPT-6b | $CH_2CH_2OH$ | H | H | H |
| HPT-6c | $C_8H_{17}$ | H | H | H |

Type (HPT-II)

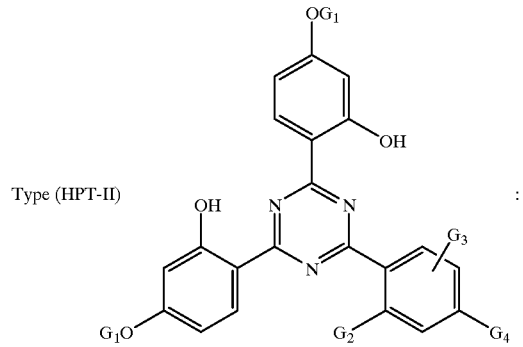

| No. | $G_1$ | $G_2$ | $G_4$ | $G_3$ |
|---|---|---|---|---|
| HPT-7 | $C_{18}H_{37}$ | $CH_3$ | $CH_3$ | o-$CH_3$ |
| HPT-8 | $CH_2CH(OH)CH_2O-C_4H_9(n)$ | H | H | H |
| HPT-9 | $CH_2CH(OH)CH_2O-C_4H_9(n)$ | $CH_3$ | $CH_3$ | H |
| HPT-10 | $CH_2CH(OH)CH_2O-C_4H_9(n)$ | $CH_3$ | $CH_3$ | o-$CH_3$ |
| HPT-11 | $CH_2CH(OH)-C_4H_9(n)$ | $CH_3$ | $CH_3$ | o-$CH_3$ |
| HPT-12 | $CH(OH)-C_5H_{11}(n)$ | $CH_3$ | $CH_3$ | o-$CH_3$ |
| HPT-13 | $C_8H_{17}$ | H | Cl | H |
| HPT-14 | $CH(CH_3)-COO-C_2H_5$ | $CH_3$ | $CH_3$ | o-$CH_3$ |
| HPT-15 | $CH_2CH(OCOCH_3)CH(C_2H_5)-C_4H_9(n)$ | H | H | H |
| HPT-16 | $CH_2CH(OH)CH(C_2H_5)-C_4H_9(n)$ | H | H | H |
| HPT-17 | $CH_2CH_2-O-CO-C(CH_3)_3$ | H | H | H |
| HPT-18 | H | H | H | H |
| HPT-19 | $(CH_2)_{10}COO-C_2H_5$ | H | Cl | H |
| HPT-20 | $(CH_2)_5COOH$ | H | H | H |
| HPT-21 | $CH_2CH(C_2H_5)-C_4H_9(n)$ | H | H | H |
| HPT-22 | $CH_2CH(OH)CH_2-O-C_4H_9(n)$ | H | t-$C_4H_9$ | H |
| HPT-23 | $CH_2CH(OH)CH_2-O-C_4H_9(n)$ | H | $OCH_3$ | H |
| HPT-24 | $(CH_2)_3-Si(CH_3)_3$ | H | H | H |

Type (HPT-III)

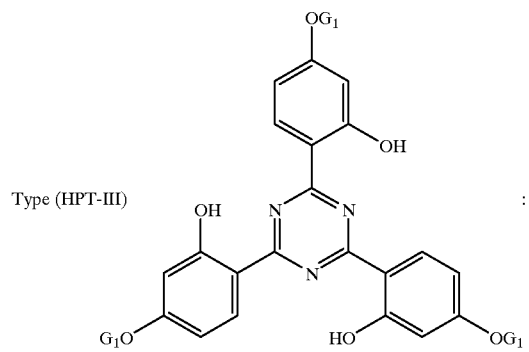

| No. | G$_1$ |
|---|---|
| HPT-26 | cyctohexyl |
| HPT-26a | (structure: 2-methyl-4-vinyl-cyclohexanol) |
| HPT-26b | CH$_2$CH(OH)CH$_2$—O-2-butyl/2-pentyl (mixture) |
| HPT-27 | CH$_2$CH(OH)CH$_2$—O—C$_4$H$_9$(n) |
| HPT-28 | (CH$_2$)$_{10}$COO—C$_2$H$_5$ |
| HPT-29 | CH$_2$CH(OH)CH(C$_2$H$_5$)—C$_4$H$_9$(n) |
| HPT-30 | C$_4$H$_9$ |
| HPT-31 | CH$_2$CH(OH)CH$_2$—O-ethyl/isopropyl/C$_4$H$_9$(n) (mixture) |
| HPT-32 | CH(C$_3$H$_7$)$_2$ |
| HPT-33 | cyclopentyl |
| HPT-34 | CH$_2$CH(OH)CH$_2$—O—CH$_2$CH$_2$—O—CH(CH$_3$)C$_2$H$_5$ |
| HPT-49 | (structure: 2-methylcyclohexanol) |
| HPT-50 | (structure: 2-methylcyclohexyl acetate) |
| HPT-51 | C(CH$_3$)$_2$—COO—C$_2$H$_5$ |
| HPT-52 | CH(CH$_3$)—COO—C$_2$H$_5$ |
| HPT-53 | CH$_2$CH(OH)CH$_2$—O—CH(CH$_3$)—C$_2$H$_5$/C$_3$H$_7$ |
| HPT-54 | (CH$_2$)$_5$—CH$_3$ |

Type (HPT-IV)

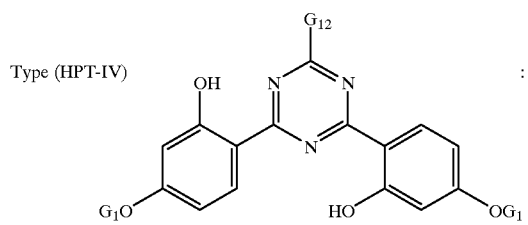

| No. | G$_1$ | G$_{12}$ |
|---|---|---|
| HPT-35 | CH$_3$ | OCH$_2$CH$_2$OC$_2$H$_5$ |
| HPT-36 | CH$_2$CH(OCOCH$_3$)CH(C$_2$H$_5$)—C$_4$H$_9$(n) | OCH$_3$ |
| HPT-37 | CH$_2$CH$_2$CH$_2$—O—CO—C$_2$H$_5$ | OCH$_3$ |
| HPT-38 | CH$_2$CH(OH)CH$_2$—O—C$_4$H$_9$(n) | CH$_3$ |
| HPT-39 and | CH$_2$CH(OH)CH$_2$—O—C$_4$H$_9$(n) | OCH$_3$ |

-continued
HPT-41
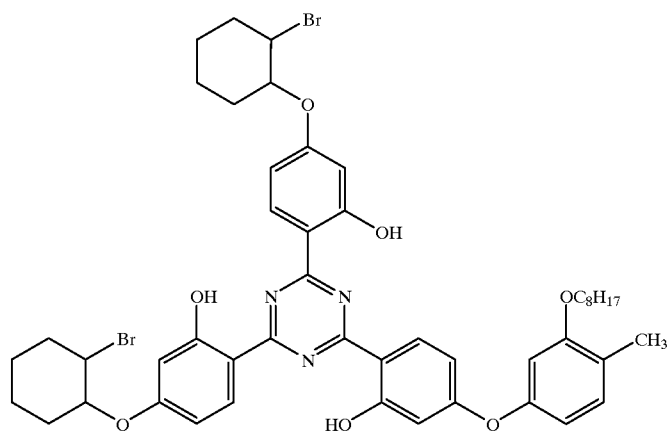
HPT-42
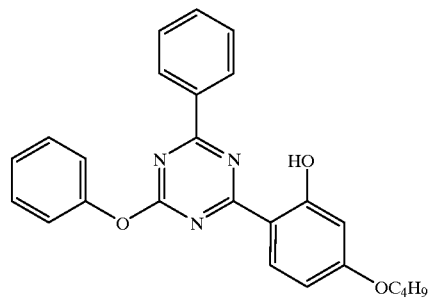
Type (HPT-V)
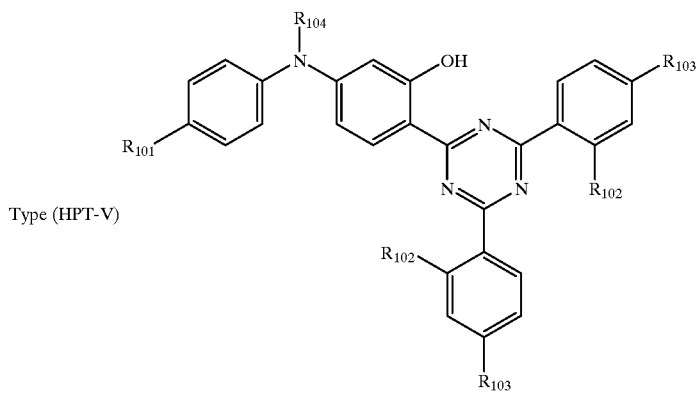
| No. | $R_{101}$ | $R_{102}$ | $R_{103}$ | $R_{104}$ |
|---|---|---|---|---|
| HPT-43 | H | H | H | H |
| HPT-44 | H | $CH_3$ | $CH_3$ | H |
| HPT-45 | H | OH | H | H |
| HPT-46 | H | OH | H | $CH_3$ |
| HPT-47 | H | $OCH_3$ | $OCH_3$ | H |
| HPT-48 | $CH_3$ | H | H | H |
Abbreviations used in above formulae:
i=isomer mixture; n=straight-chain radical; t=tertiary radical; o-, m- and p- denote the position of the radical relative to the triazine ring.
Of emphasized general interest are compounds of the formula (HPT-IIIA)

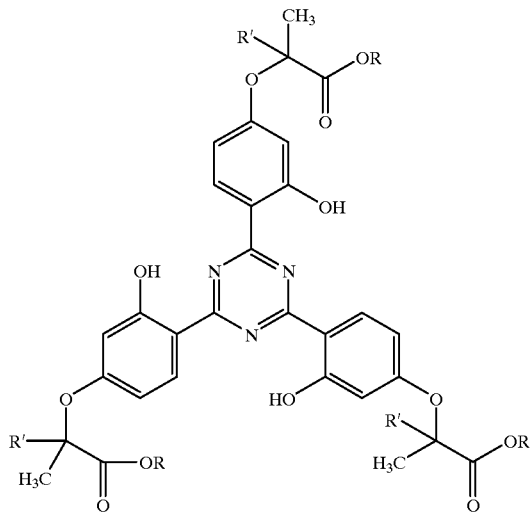

wherein R and R' independently are H, methyl or ethyl; preferred are those wherein R is methyl or ethyl. These compounds are effective as stabilizers for all kinds of organic material; they can be applied in the manner described above for compounds of the formula I. Preferred compounds are the following:

a. 2,4,6-tris(4-[1-ethoxycarbonyl-1-methylethoxy]-2-hydroxyphenyl)-1,3,5-triazine;
b. 2,4,6-tris(4-[1-methoxycarbonyl-1-methylethoxy]-2-hydroxyphenyl)-1,3,5-triazine;
c. 2,4,6-Tris(2-hydroxy-4-(1-ethoxycarbonylpropoxy)phenyl)-1,3,5-triazine;
d. 2,4,6-Tris(2-hydroxy-4-(1-methoxycarbonylpropoxy)phenyl)-1,3,5-triazine;
e. 2,4,6-Tris(2-hydroxy-4-(1-ethoxycarbonylethoxy)phenyl)-1,3,5-triazine;
f. 2,4,6-Tris(2-hydroxy-4-(1-methoxycarbonylethoxy)phenyl)-1,3,5-triazine.

These novel compounds are especially useful as part of a stabilizer combination, e.g. with compounds of the formula I, further hydroxyphenyltriazines and/or benztriazoles.

Benzotriazole compounds of the formula AII (AII)

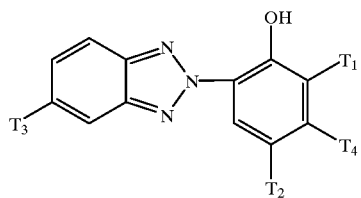

in which $T_1$ and $T_2$ independently of one another are hydrogen, halogen, alkyl, alkyl substituted by $COOT_5$, alkoxy, aryloxy, hydroxyl, aralkyl, aryl or acyloxy, where $T_5$ is alkyl or alkyl interrupted by one or more O, or $T_1$ is a group of the formula

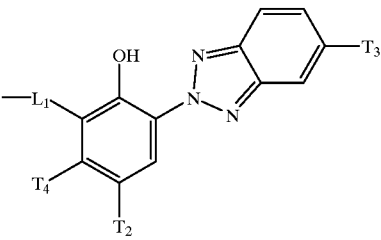

in which $L_1$ is a bivalent group, for example $-(CH_2)_n-$ where n is from the range 1–8, $T_3$ is hydrogen, halogen, alkyl, alkoxy, aryloxy, acyloxy; $-CF_3$, phenyl, $-S-T_6$, $-SO_2-T_6$; and $T_4$ is hydrogen, hydroxyl, alkoxy, aryloxy or acyloxy or a group of one of the formulae $-OCH_2CH(OT_8)-CH_2-O-T_7$ or $-OCH_2CH_2-O-CO-T_7$;

$T_6$ is alkyl or aryl;

$T_7$ is alkyl or aryl;

$T_8$ is hydrogen or $CO-T_9$;

$T_9$ is alkyl or alkenyl;

and polymers prepared using these compounds. Preference is given to those compounds of the formula A II which are liquid in the temperature range around 20° C. or form a liquid phase in a mixture with other substances, especially to those in which $T_1$ and $T_2$ independently of one another are hydrogen, halogen, alkyl, alkyl substituted by $COOT_5$, alkoxy, aryloxy, hydroxyl, aralkyl, aryl or acyloxy, where $T_5$ is alkyl or alkyl which is interrupted by one or more O.

Within the scope of the stated definitions $T_1$, $T_2$, $T_3$ and $T_4$ may also carry additional substituents, for example an ethylenically unsaturated, polymerizable group. Dimers or polymers are also possible.

Especial preference is given to those compounds of the formula AII, in which $T_1$ is H, $C_1$–$C_{12}$alkyl, 1,1-dimethylbenzyl;

$T_2$ is H, $C_1$–$C_{12}$alkyl, 1,1-dimethylbenzyl or $CH_2CH_2COOT_5$;

$T_3$ is chlorine, $CF_3$, $-S-T_6$, $-SO_2-T_6$;

$T_4$ is hydrogen or $C_1$–$C_{18}$alkoxy;

$T_5$ is $C_1$–$C_{18}$alkyl, or $C_3$–$C_{18}$alkyl interrupted by one or more O; and $T_6$ is phenyl.

The radicals designated as alkyl, alkenyl, aryl, arylalkyl, acyl, alkyloxy, alkenyloxy, aryloxy, arylalkyloxy and acyloxy for the conventional UV absorbers are generally those which are common in the art; preferred radicals are generally—as regards chain length, number of carbon atoms and any heteroatoms etc.—of the type as defined above for the novel compounds of the formula (I).

Examples of benzotriazoles (HBT) of the formula AII are:

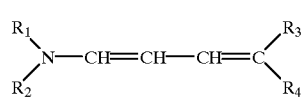

| HBT-No. | $T_1$ | $T_2$ | $T_3$ | $T_4$ |
|---|---|---|---|---|
| HBT-1 | H | $CH_3$ | H | H |
| HBT-2 | H | $C(CH_3)_3$ | H | H |
| HBT-3 | $C(CH_3)_3$ | $CH_3$ | Cl | H |
| HBT-4 | $C(CH_3)_3$ | $C(CH_3)_3$ | Cl | H |
| HBT-5 | $C(CH_3)_2C_2H_5$ | $C(CH_3)_2C_2H_5$ | H | H |
| HBT-6 | $CH(CH_3)C_2H_5$ | $C(CH_3)_3$ | H | H |
| HBT-7 | $C(CH_3)_2$—Ph | $C(CH_3)_2$—Ph | H | H |
| HBT-8 | $C(CH_3)_3$ | $CH_2CH_2COOC_8H_{17}$ (isomers) | Cl | H |
| HBT-9 | $C(CH_3)_3$ | $CH_2CH_2COOC_8H_{17}$ (isomers) | H | H |
| HBT-10 | $C_{12}H_{25}$ (isomers)* | $CH_3$ | H | H |
| HBT-11 | $C(CH_3)_2$—Ph | —$C(CH_3)_2$—$C(CH_3)_3$ | H | H |
| HBT-12 | H | H | H | $O(CH_2)_2$—O—CO—$C(CH_3)$=$CH_2$ |
| HBT-13 | H | H | Cl | (methacrylate glyceryl acetate group) |
| HBT-14 | H | H | H | (glyceryl ether group) |
| HBT-15 | sec-$C_4H_9$ | sec-$C_4H_9$ | Cl | H |

*principal product

Other suitable UV absorbers are those of the formula AIII

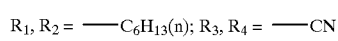

(AIII)

in which $R_1, R_2 =$ —$C_6H_{13}(n)$; $R_3, R_4 =$ —CN $R_1, R_2 =$ —$C_2H_5$; $R_3 =$ —$SO_2$—Ph;

$R_4 =$ —CO—$OC_8H_{17}$

-continued $R_1, R_2 =$ —$C_2H_5$; $R_3 =$ —$SO_2$—Ph;

$R_4 =$ —COO—$C_{12}H_{25}$ $R_1, R_2 =$ —$CH_2$=CH—$CH_2$; $R_3, R_4 =$ —CN

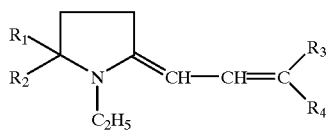

$R_1, R_2 =$ H; $R_3 =$ —CN; $R_4 =$ —CO—$NHC_{12}H_{25}$ $R_1, R_2 =$ —$CH_3$; $R_3 =$ —CN; $R_4 =$ —CO—$NHC_{12}H_{25}$

-continued
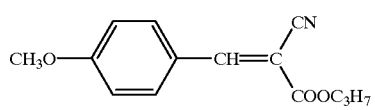
Other substances which can be used as light or dark stabilizers are described in U.S. Pat. No. 5,580,710 or U.S. Pat. No. 5,543,276.
Examples of particularly suitable compounds are:
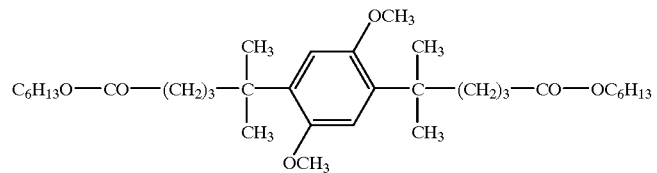
(ST-1)
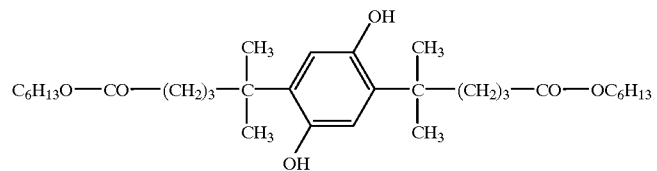
(ST-2)
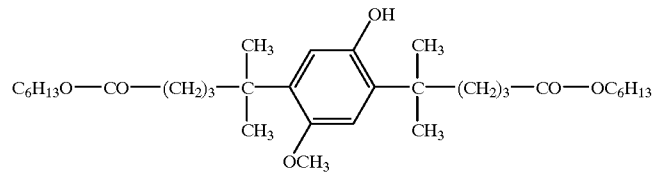
(ST-3)
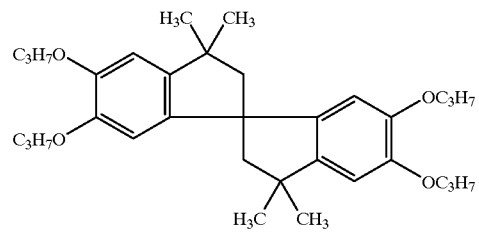
(ST-4)
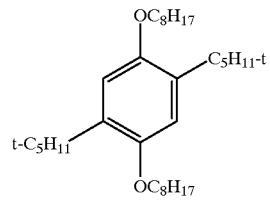
(ST-5)
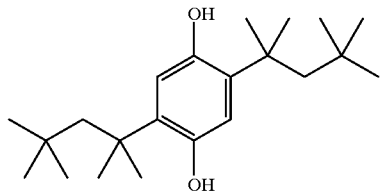
(ST-6)

-continued
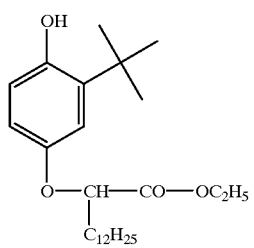
(ST-7)
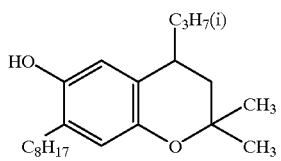
(ST-8)
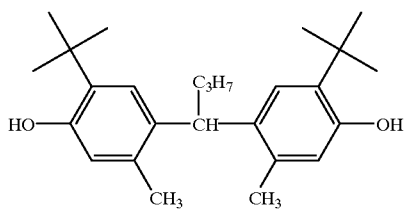
(ST-9)
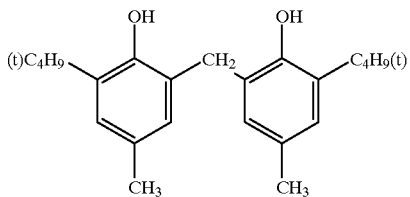
(ST-10)
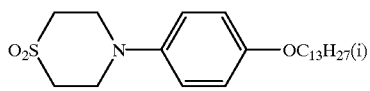
(ST-11)
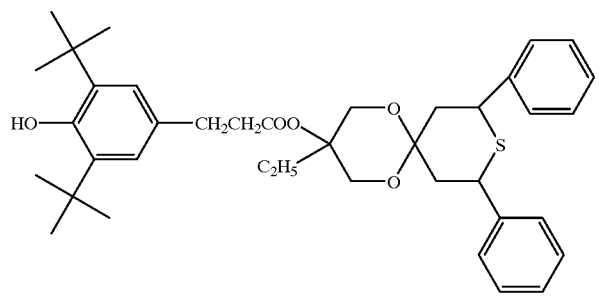
(ST-12)
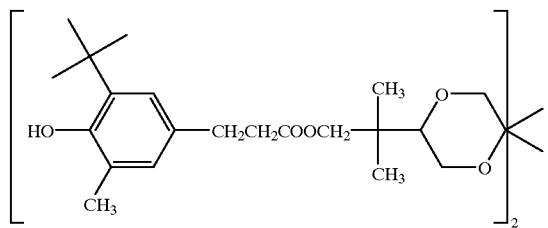
(ST-13)

(ST-14)
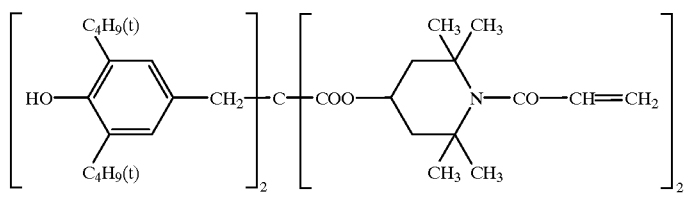
(ST-15)
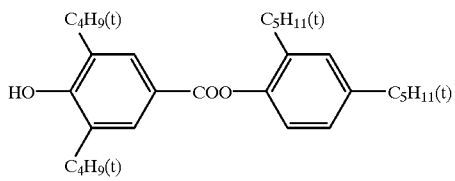
(ST-16)
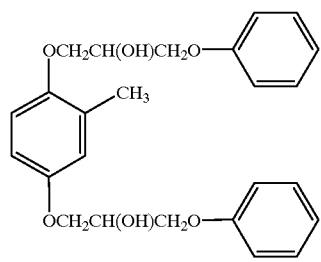
(ST-17)
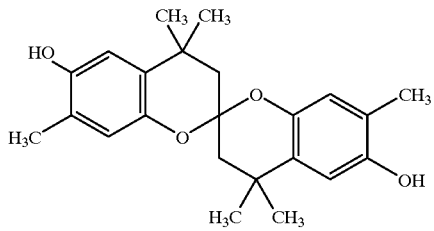
(ST-18)
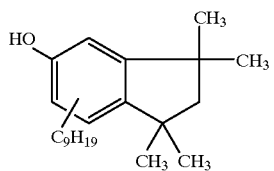
(ST-19)
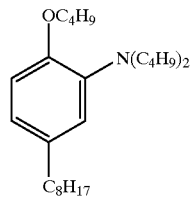

(ST-20)
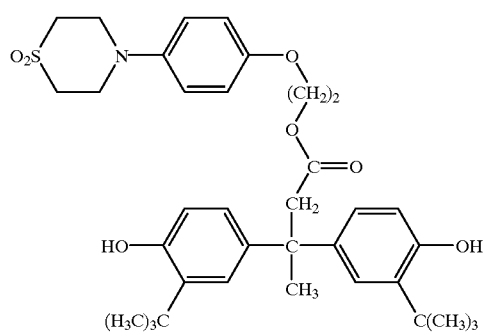
(ST-21)
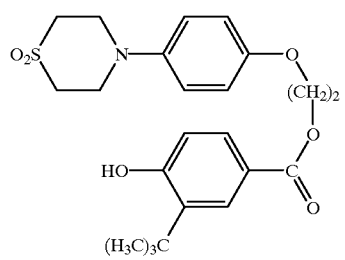
(ST-22)
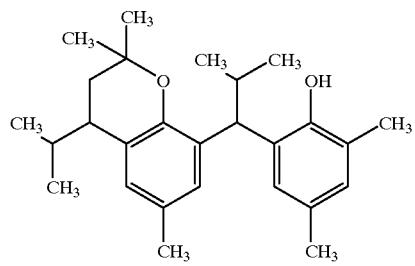
(ST-23)
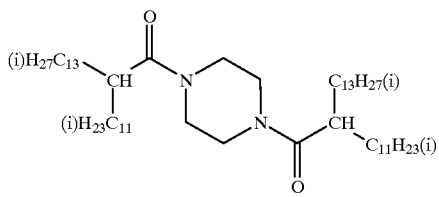
(ST-24)
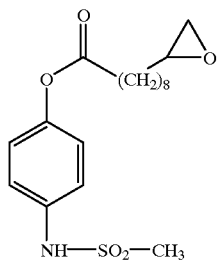

(ST-25)

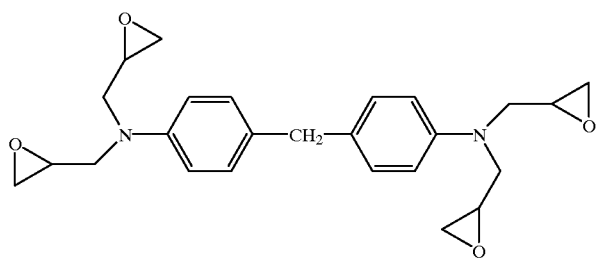

(ST-26)

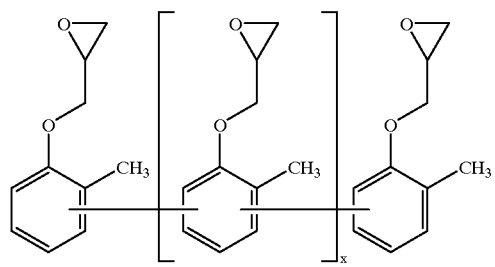

Further details on the structure of colour photographic material, and the components which can be employed in the novel material, can be found, inter alia, in U.S. Pat. No. 5,538,840, column 27, line 25, to column 106, line 16, and in the publications cited therein; these passages of U.S. Pat. No. 5,538,840 are hereby incorporated by reference. Further important components, especially couplers, are described in U.S. Pat. No. 5,578,437.

The present invention additionally provides a method of stabilizing photographic recording material comprising, on a base, at least one silver-halide emulsion layer and, if desired, at least one interlayer and/or one protective layer, which comprises adding a UV absorber of the formula (I) to at least one of the said layers.

The present invention also provides for the use of compounds of the formula (I) for stabilizing photographic recording material comprising, on a base, at least one silver halide emulsion layer and, if desired, at least one interlayer and/or one protective layer.

The preferences described earlier above in connection with the novel compounds of the formula (I) apply analogously to the novel compositions, the novel method and the novel use.

Incorporation into the organic material to be stabilized can take place, for example, by mixing or applying the compounds of the formula I and any other additives by methods customary in the art. Where the materials are polymers, especially synthetic polymers, incorporation can take place prior to or during shaping, or by applying the dissolved or dispersed compound to the polymer, with or without subsequent evaporation of the solvent. In the case of elastomers, these can also be stabilized as latices. A further option for incorporating the compounds of the formula I into polymers is to add them prior to, during or directly after the polymerization of the corresponding monomers and/or prior to crosslinking. In this context the compounds of the formula I can be added as they are or else in encapsulated form (for example in waxes, oils or polymers). In the case of addition prior to or during polymerization the compounds of the formula I may also act as a regulator of the chain length of the polymers (chain terminators).

The compounds of the formula I can also be added in the form of a masterbatch which contains this compound, for example, in a concentration of from 2.5 to 25% by weight, to the polymers that are to be stabilized.

The compounds of the formula I can judiciously be incorporated by the following methods:

as an emulsion or dispersion (e.g. to latices or emulsion polymers), as a dry mix during the mixing in of additional components or polymer mixtures, by direct addition to the processing apparatus (e.g. extruders, internal mixers etc.)

as a solution or melt.

The stabilized polymer compositions obtained in this way can be converted into shaped articles, for example into fibres, films, tapes, sheets, sandwich boards, vessels, pipes and other profiles, by the customary methods, for example by hot pressing, spinning, extrusion or injection moulding.

The invention therefore also provides for the use of the novel polymer composition for producing a shaped article.

The examples which follow describe the invention further without constituting any restriction. Parts and percentages therein are by weight; an example which mentions room temperature means thereby a temperature in the range 20–25° C. In the case of solvent mixtures such as those for chromatography the parts indicated are by volume. These definitions apply unless specified otherwise. The following abbreviations are used:

| | |
|---|---|
| THF | tetrahydrofuran |
| abs. | andydrous |
| m.p. | melting point or melting range |
| NMR | nuclear magnetic resonance |
| torr = | torricelli; mmHg (1 torr is about 133 Pa) |
| $T_g$ | glass transition temperature; |
| h: | hours. |

EXAMPLE 1

2,4,6-tris(4-[1-ethoxycarbonyl-1-methylethoxy]-2-hydroxyphenyl)-1,3,5-triazine (Compound 1)

A mixture of 203 g (0.50 mol) of 2,4,6-tris(2,4-dihydroxyphenyl)-1,3,5-triazine, 644 g (3.30 mol) of ethyl α-bromoisobutyrate (Fluka, 97%) and 112 g (1.65 mol) of sodium ethoxide (Fluka, >95%) in 1.00 l of anhydrous ethanol (Fluka, >99.8%, absolute) is heated to 78° C. under nitrogen and with stirring. After intervals of 1.5 h, 3.5 h and 4.5 h 37.4 g (0.55 mol) of sodium ethoxide (Fluka, >95%) are added to this reaction mixture. After 6 h it is cooled to 25° C. and poured into 1.00 l of 2% hydrochloric acid. The aqueous phase is extracted with ethyl acetate and the organic phase is dried over magnesium sulfate. The solvent is removed in vacuo and the title product is obtained following crystallization from isopropanol, as a pale yellow powder (melting point 150° C.).

EXAMPLE 2

2,4,6-tris(4-[1-methoxycarbonyl-1-methylethoxy]-2-hydroxyphenyl)-1,3,5-triazine (Compound 2).

A mixture of 40.5 g (0.100 mol) of 2,4,6-tris(2,4-dihydroxyphenyl)-1,3,5-triazine, 119 g (0.660 mol) of methyl α-bromoisobutyrate (Fluka, 97%) and 17.8 g (0.330 mol) of sodium methoxide (Fluka, >95%) in 1.00 l of anhydrous methanol (Fluka, >99,8%, absolute) is heated to 78° C. under nitrogen and with stirring. After 2 h 17.8 g (0.330 mol) of sodium methoxide (Fluka, >95%) are added to this reaction mixture. After 16 h it is cooled to 25° C. and poured into 1.00 l of 2% hydrochloric acid. The aqueous phase is extracted with ethyl acetate and the organic phase is dried over magnesium sulfate. The solvent is removed in vacuo and the title product is obtained after column chromatography on silica gel (Fluka, size 60 silica gel, 0.040–0.063 mm) with 20:1 chloroform ethyl/acetate, as a pale yellow powder (melting point 131° C.).

EXAMPLE 3

2,4,6-Tris(2-hydroxy-4-(1-ethoxycarbonylpropoxy)phenyl)-1,3,5-triazine 10.1 g (0.025 mol) of 2,4,6-tris(2,4-dihydroxyphenyl)-1,3,5-triazine are added to a solution of 5.6 g (0.0825 mol) of sodium ethylate in 70 ml of absolute ethanol, which mixture then turns red. After heating the mixture to reflux temperature, 16.1 g (0.0825 mol) of ethyl 2-bromobutyrate are added dropwise. After 4 hours, the mixture is filtered hot, the solvent is removed by evaporation and the residue is taken up in 350 ml of ethyl acetate. After washing the organic phase with water, aqueous HCl solution and then again with water, it is dried using $MgSO_4$ and the solvent is removed by evaporation. The residue is chromatographed with hexane/ethyl acetate over silica gel, giving a compound of the following structure (m.p. 101–105° C.):

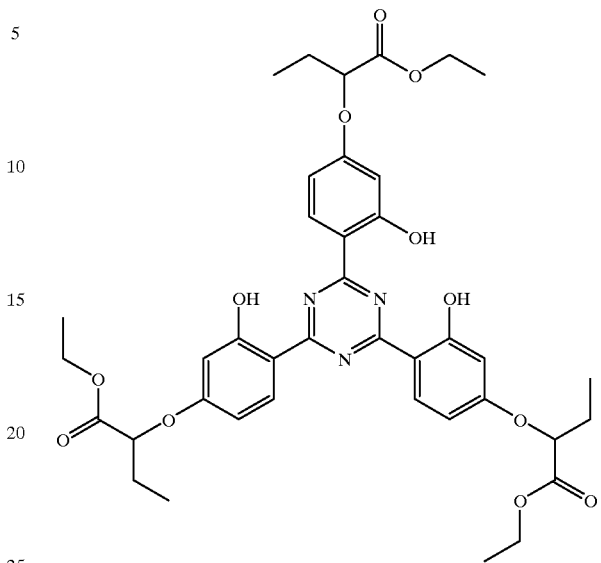

EXAMPLE 4
2,4,6-Tris(2-hydroxy-4-(1-ethoxycarbonylethoxy)phenyl)-1,3,5-triazine 40.5g (0.100 mol) of 2,4,6-tris(2,4-dihydroxyphenyl)-1,3,5-triazine and 42.8g (0.310 mol) of anhydrous $K_2CO_3$ are suspended at 50° C. in 250 ml of dimethyl-formamide. After 30 minutes, 45.1 g (0.330 mol) of ethyl 2-chloropropionate are added and the mixture is stirred for another 14 h. The reaction mixture is filtered hot and the solvent is removed under vacuum. The residue is dissolved in 300 ml of dichloromethane and washed with water, aqueous HCl and again with water, dried using $MgSO_4$ and concentrated by evaporation. The residue is chromatographed over silica gel, giving a product of the following structure (m.p. 115–120° C.):

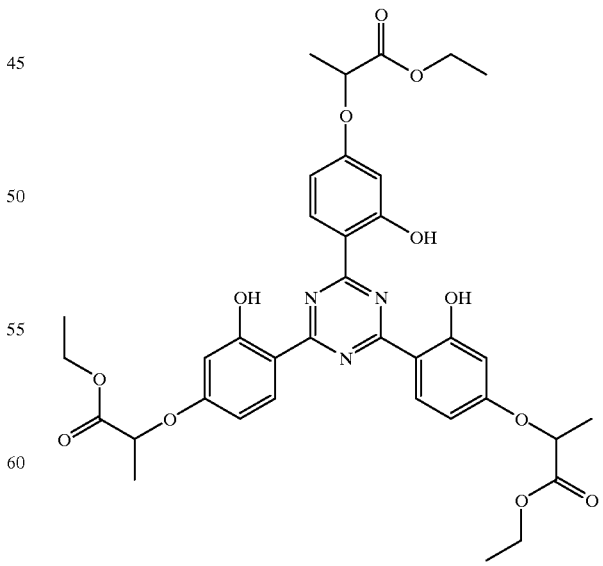

EXAMPLE 5

2,4,6-Tris(2-hydroxy-4-(1-methoxycarbonylethoxy) phenyl)-1,3,5-triazine

The methyl ester is prepared in analogy to the procedure of Example 4 (m.p. 145–147° C.).

Use Examples

EXAMPLE 6 a) Impregnation: Relative to the weight of the total formulation 0.5% of the additives indicated in Table 1 below is added to a commercially available impregnant (Xylamon Incolore™; Manufacturer: Sepam).

The impregnant is applied by brush to spruce boards (one application) and dried at room temperature for 24 hours.

b) Topcoat: A topcoat is prepared from:

- 53.48 parts by weight of alkyd resin (Jägalyd Antihydro™, E. Jäger KG, 60% solution in white spirit);
- 10.69 parts by weight of a thixotropic auxiliary (Jägalyd Antihydro-Thix™, E. Jäger KG, 50% solution);
- 1.92 parts by weight of accelerator (Jäger Antihydro-Trockner™);
- 33.44 parts by weight of solvent (Terlitol™30);
- 0.32 part by weight of anti-skinning agent (Ascinin™ P, BAYER);
- 0.15 part by weight of anti-skinning agent (Luactin™ M, BASF).

The topcoat is stabilized by adding 1.0% of novel UV absorber of the formula HPT-IIIA and 1.0% of the compound of formula

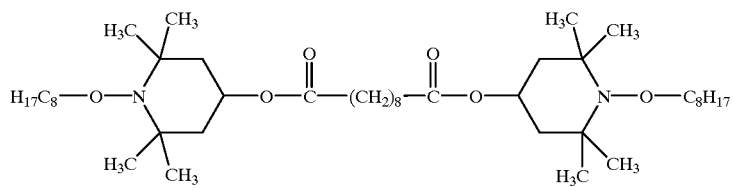

(hindered amine-type light stabilizer, Ciba Specialty Chemicals), the amounts being based in each case on the solids content of the binder. A comparative specimen is prepared without the addition of these stabilizers.

The topcoat is applied by brush (3 applications) to the impregnated spruce boards, which are dried at room temperature for 24 hours after each application.

The specimens are subsequently subjected to accelerated weathering: UV-A lamps with maximum light intensity at 340 nm; weathering cycle: 5 h of light at 58° C., 1 h of spraying at 22° C.

After the stated period of weathering the colour change ΔE is determined in accordance with DIN 6174; the comparison used is an unweathered specimen with unstabilized impregnant and unstabilized topcoat. The results are collated in Table 1.

TABLE 1

Colour change ΔE in accordance with DIN 6174 on spruce, 1000 h of weathering

| Stabilizer | Colour change ΔE |
|---|---|
| None | 28.3 |
| Compound No. 1 | 18.3 |

EXAMPLE 7

Stabilization of a 2-coat metallic paint

The test compound is incorporated into 30 g of Solvesso®100[4]) and tested in a clearcoat of the following composition (parts by weight):

| | |
|---|---|
| Synthacryl ® SC 303[1]) | 27.51 |
| Synthacryl ® SC 370[2]) | 23.34 |
| Maprenal ® 650[3]) | 27.29 |
| Butylacetate/butanol (37/8) | 4.33 |
| Isobutanol | 4.87 |
| Solvesso ® 150[4]) | 2.72 |

-continued

| | |
|---|---|
| Kristollöl K-30[5]) | 8.74 |
| Levelling assistant Baysilon ® MA[6]) | 1.2 |

[1])Acrylate resin from Hoechst AG; 65% solution in xylene/butanol (26/9)
[2])Acrylate resin from Hoechst AG: 75% solution in Solvesso ® 100[4])
[3])Melamine resin from Hoechst AG; 55% solution in isobutanol
[4])Mixture of aromatic hyrdrocarbons (Manufacturer: Esso); boiling range 182–203° C. (Solvesso ® 150) or 161–178° C. (Solvesso ® 100)
[5])Mixture of aliphatic hydrocarbons (Manufacturer: Shell); boiling range 145–200° C.
[6])(1% in Solvesso ® 150[4]) (Manufacturer; Bayer AG)

1.0% by weight of the compound of present invention is added to the clearcoat; in some samples, an additional 0.7% of the compound of the formula

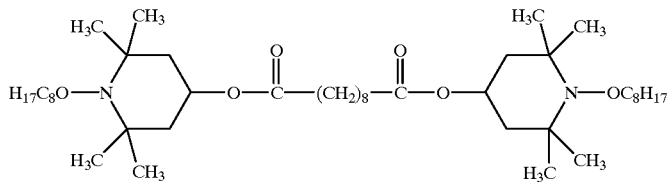

(Compound A) is incorporated (amounts based in each case on the solids content of the coating material). The comparison material used is a clearcoat containing no light stabilizer.

The clearcoat is diluted to spray viscosity with Solvesso®100 and applied by spraying to a prepared aluminium panel (Uniprime® Epoxy, red metallic basecoat) and the painted panel is baked at 130° C. for 30 minutes. The result is a clearcoat dry-film thickness of 40–50 μm.

The samples are then weathered in an UVCON® weathering device from Atlas Corp. (UVB-313 lamps) with a cycle of 4 h of UV irradiation at 70° C. and 4 h condensation at 50° C.

The samples are examined at regular intervals for gloss (200 gloss as per DIN 67530) and freedom from cracking; before the beginning of weathering a gloss value of 94 is measured. The results are collated in Table 2 below.

TABLE 2

20° gloss as per DIN 67530 after 2400 h of weathering

| Stabilizers Compd. A | HPT-IIIA | 20° gloss |
|---|---|---|
| none | none | — (crack after 1600 h) |
| 1% A | none | 44 |
| 1% A | 1% Compd. 1 | 87 |

The samples that are stabilized in accordance with the invention exhibit excellent gloss retention and freedom from cracking.

What is claimed is:

1. A compound of the formula (HPT-IIIA)

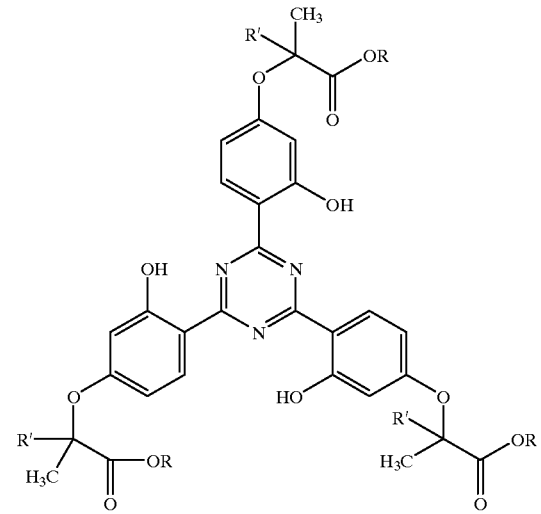

wherein R and R' independently are H, methyl or ethyl.

2. A compound of the formula (HPT-IIIA) according to claim 1 wherein R is methyl or ethyl.

3. A compound selected from the compounds a–f:
   a. 2,4,6-tris(4-[1-ethoxycarbonyl-1-methylethoxy]-2-hydroxyphenyl)-1,3,5-triazine;
   b. 2,4,6-tris(4-[1-methoxycarbonyl-1-methylethoxy]-2-hydroxyphenyl)-1,3,5-triazine;
   c. 2,4,6-Tris(2-hydroxy-4-(1-ethoxycarbonylpropoxy)phenyl)-1,3,5-triazine;
   d. 2,4,6-Tris(2-hydroxy-4-(1-methoxycarbonylpropoxy)phenyl)-1,3,5-triazine;
   e. 2,4,6-Tris(2-hydroxy-4-(1-ethoxycarbonylethoxy)phenyl)-1,3,5-triazine;
   f. 2,4,6-Tris(2-hydroxy-4-(1-methoxycarbonylethoxy)phenyl)-1,3,5-triazine.

* * * * *